United States Patent [19]

Atwal et al.

[11] Patent Number: 5,140,031
[45] Date of Patent: Aug. 18, 1992

[54] PYRANYL CYANOGUANIDINE DERIVATIVES

[75] Inventors: Karnail Atwal, Newtown, Pa.; Gary J. Grover, Stockton; Kyoung S. Kim, Lawrenceville, both of N.J.

[73] Assignee: E. R. Squibb & Sons, Inc., Princeton, N.J.

[21] Appl. No.: 661,763

[22] Filed: Feb. 27, 1991

Related U.S. Application Data

[63] Continuation-in-part of Ser. No. 506,632, Apr. 9, 1990, abandoned, which is a continuation-in-part of Ser. No. 493,060, Mar. 13, 1990, abandoned, which is a continuation-in-part of Ser. No. 359,236, May 31, 1989, abandoned.

[51] Int. Cl.$^5$ .................. C07D 471/02; C07D 409/14; C07D 311/96; C07D 417/04; C07D 405/14; A61K 31/35; A61K 31/66

[52] U.S. Cl. .................................... 514/302; 514/114; 514/255; 514/392; 514/456; 514/235.5; 514/337; 540/484; 544/61; 544/151; 544/331; 544/376; 546/15; 546/22; 546/115; 546/116; 546/196; 546/269; 548/112; 548/316; 548/525; 549/345; 549/399

[58] Field of Search .................. 540/553, 546; 544/61, 544/151, 331, 376; 546/115, 116, 196, 15, 22; 548/316, 525, 112; 549/345, 399; 514/302, 114, 456, 392, 235.5, 255

[56] References Cited

U.S. PATENT DOCUMENTS 4,988,723  1/1991  Shiokawa et al. .................. 514/392

FOREIGN PATENT DOCUMENTS

| | | | |
|---|---|---|---|
| 0205292 | 6/1985 | European Pat. Off. | 549/345 |
| 214818 | 9/1985 | European Pat. Off. | 514/392 |
| 0274821 | 10/1986 | European Pat. Off. | 514/392 |
| 344747 | 6/1988 | European Pat. Off. | 549/345 |
| 0350805 | 7/1988 | European Pat. Off. | 546/115 |
| 0359537 | 9/1988 | European Pat. Off. | 546/115 |
| 389861 | 10/1990 | European Pat. Off. | 514/392 |
| WO87/07607 | 6/1986 | PCT Int'l Appl. | 546/115 |

OTHER PUBLICATIONS

V. A. Ashwood et al., "Synethsis and Antihypertensive Activity of 4-(Cyclicamido)-2H-1-benzopyrans" J. Med. Chem., 1986, 29, 2194–2201.

C. R. Rasmussen et al., "Improved Procedures of Cycloalkyl-, Arylalkyl-, and Arylthioureas", Synthesis, Jun. 1988, pp. 456–459.

V. V. Mozolis et al., "Preparation of N-Substituted Thiourea", Russian Chemical Reviews, 42 (7), 1973, pp. 587–595.

J. M. Evans et al., "Synthesis and Antihypertensive Activity of Substituted trans-4-Amino-3,4-dihydro-2,-2-dimethyl-2H-1-benzopyran-3-ols", J. Med. Chem., 1983, 26, 1582–1589.

R. W. Lang et al., "Synthesis of Selectively Trifluoromethylated Pyridine Derivatives as Potential Antihypertensives", Helvetica Chimica Acta, 1988, 71, 596–601.

P. Sebok et al., "Selective Synthesis of Analogues of the Natural Precocenes, Synthesis and Regioselective (-Alkylation of 6-Chloro- and 6-Tert-Butyl-7,-8-Dihydroxy-2,2-Dimethyl-4-Chromanones", Heterocycles, 1988, 27, 2595–2607.

P. Teixidor et al., "Improved Preparation of Precocene II, Unexpected Results in the Reduction of Alkoxy Substituted Acetophenones and 4-Chromanones with Sodium Borohydride", Heterocycles, 1988, 27, 2459–2465.

A. Banerji et al., "Enolates of o-Hydroxyacetophenones: Novel Synthesis of 2,2-Dialkyl-4-Chromanones", Tetrahedron Letters, No. 38, 1979, pp. 3685–3686.

G. Ariamala et al., "A Simple Route for the Synthesis of 4-Chlorochromenes and Chroman-4-ones", Tetrahedron Letters, vol. 29, No. 28, pp. 3487–3488 (1988).

H. J. Petersen et al., Journal of Medicinal Chemistry, vol. 21, No. 8, Aug. 1978, pp. 773–781, Washington, D.C., "Synthesis and hypotensive activity of N-alkyl-N'-cyano-N'-pyridylguanidines".

Primary Examiner—Mary C. Lee
Assistant Examiner—Joseph K. McKane
Attorney, Agent, or Firm—Theodore R. Furman, Jr.

[57] ABSTRACT

Novel compounds having the formula

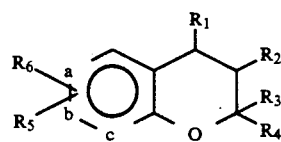

wherein

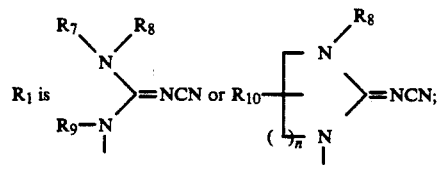

are disclosed. These compounds have potassium channel activating activity and are useful, for example, as cardiovascular agents, especially as antiischemic agents.

35 Claims, No Drawings

PYRANYL CYANOGUANIDINE DERIVATIVES

This is a continuation-in-part of co-pending application Ser. No. 506,632 filed Apr. 9, 1990, now abandoned, which is a continuation-in-part of Ser. No. 493,060 filed Mar. 13, 1990, abandoned, which is a continuation-in-part of co-pending application Ser. No. 359,236 filed May 31, 1989, abandoned.

FIELD OF THE INVENTION

The present invention relates to novel compounds having potassium channel activating activity which are therefore useful, for example, as cardiovascular agents.

SUMMARY OF THE INVENTION

In accordance with the present invention novel compounds having potassium channel activating activity which are useful, for example, as cardiovascular agents, are disclosed. These compounds have the general formula

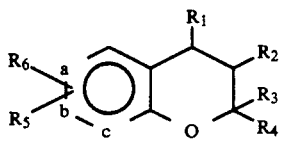

wherein a, b, and c are all carbons or one of a, b and c can be nitrogen or —NO— and the others are carbons;

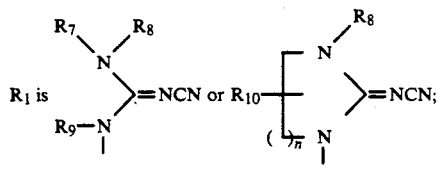

$R_2$ is hydrogen, hydroxy,

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

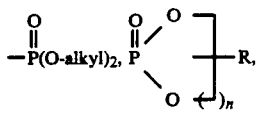

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, haloalkyl, aryl, arylalkyl, cycloalkyl, or (cycloalkyl)alkyl;

$R_6$ is selected from H, alkyl, OH, O-alkyl, amino, substituted amino, NHCOR (wherein R is as defined above), CN, and NO$_2$;

$R_7$ and $R_8$ are each independently selected from hydrogen, alkyl, alkenyl, aryl, (heterocyclo)alkyl, heterocyclo, arylalkyl, cycloalkyl and (cycloalkyl)alkyl, substituted alkyl wherein the substituents include alkoxy, alkylthio and substituted amino, or $R_7$ and $R_8$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R_9$ and $R_{10}$ are selected from hydrogen, alkyl, alkenyl, aryl, arylalkyl, cycloalkyl or cycloalkylalkyl; or $R_{10}$ can be an aryl group fused to 2 carbon atoms of the cyanoguanidine ring portion; and n is 1, 2 or 3.

DETAILED DESCRIPTION OF THE PRESENT INVENTION

This invention in its broadest aspects relates to the cyanoguanidine compounds of formula I above, to compositions and the methods of using such compounds. The compounds of formula I are useful, for example, as cardiovascular agents. Preferred compounds are those with the 3S, 4R stereochemistry.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and one double bond, preferably three to five carbons. The term "alkynyl" refers to straight or branched chain hydrocarbon radicals having from two to eight carbons and one triple bond, preferably three to five carbons.

The term "cycloalkyl" refers to saturated carbocyclic rings of 3 to 7 carbon atoms with cyclopropyl, cyclopentyl and cyclohexyl being most preferred.

The term "halo" or "halogen" refers to chloro, bromo and fluoro.

The term "halo substituted alkyl" refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons,

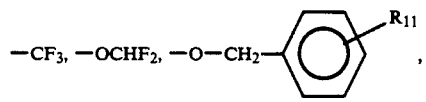

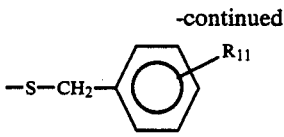

(wherein R$_{11}$ is hydrogen, alkyl of 1 to 4 carbons, alkoxy of 1 to 4 carbons, alkylthio of 1 to 4 carbons, halo, hydroxy or CF$_3$), —O—CH$_2$—cycloalkyl, or —S—CH$_2$— cycloalkyl, and di-substituted phenyl, 1-naphthyl, 2-naphthyl wherein said substituents are selected from methyl, methoxy, methylthio, halo, CF$_3$, nitro, amino, and OCHF$_2$.

Preferred aryl groups include unsubstituted phenyl and monosubstituted phenyl wherein the substituents are nitro, halo, —CF$_3$, alkyl, cyano or methoxy.

The term "heterocyclo" refers to fully saturated or unsaturated rings of 5 or 6 atoms containing one or two 0 and S atoms and/or one to four N atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —N-H—alkyl wherein alkyl is of 1 to 4 carbons, —N(alkyl)$_2$ wherein alkyl is of 1 to 4 carbons, CF$_3$, or OCHF$_2$ or such monocyclic and bicyclic rings wherein two or three available carbons have substituents selected from methyl, methoxy, methylthio, halo, CF$_3$, nitro, hydroxy, amino and OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

The compounds of formula I wherein R$_1$ is

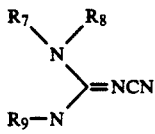

can be prepared by treatment of a thiourea of the formula

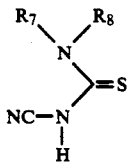

with an amine of the formula

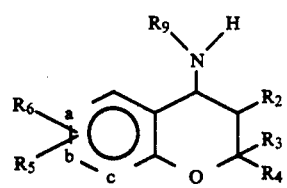

in the presence of a coupling agent, such as a carbodiimide, in a solvent, such as dimethylformamide, tetrahydrofuran, acetonitrile or dichloromethane. If dicyclohexylcarbodiimide is used, it should be employed with an acid source. Preferably, the carbodiimide is of the formula

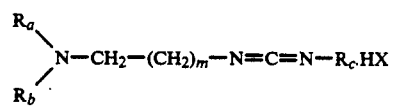

wherein X is halogen, R$_a$, R$_b$ and R$_c$ are independently alkyl, cycloalkyl, phenyl, phenylalkyl, cycloalkylalkyl or R$_a$ and R$_b$ together with the N-atom form 1-pyrrolidinyl, 1-piperidinyl, 4-morpholinyl, 4-thiomorpholinyl, 4-alkyl-1-piperazinyl or 4-phenylalkyl-1-piperazinyl. Most preferably the carbodiimide is 1-(3-dimethylaminopropyl)-3-ethylcarbodiimide hydrochloride.

The thiourea of formula II, wherein R$_8$ is hydrogen can be prepared by heating an isothiocyanate of the formula

R$_7$N=C=S                 IV with either monosodium cyanamide or with cyanamide in the presence of an organic base, such as triethyl amine.

The other thioureas of formula II can be prepared by standard methods described in the literature, such as by C. R. Rasmussen, F. J. Villani, Jr., L. E. Weaner, B. E. Reynolds, A. R. Hood, L. R. Hecker, S. O. Nortey, A. Hanslin, M. J. Costanzo, E. T. Powell, A. J. Molinari, *Synthesis*, 1988, p. 456, and V. V. Mozolis and S. P. Locubaitite, *Russian Chemical Reviews*, 1973, 42, 587.

The aminoalcohol of formula III wherein R$_2$ is hydroxy can be prepared by methods described in the literature, such as by J. M. Evans, C. S. Fake, T. C. Hamilton, R. H. Poyser, E. A. Watts, *J. Med. Chem.* 1983, 26, 1582 and *J. Med. Chem.* 1986, 29, 2194; R. W. Lang, P. F. Wenk, *Helvetica Chimica Acta*, 1988, 71, 596; EP 0205292 A2 (1986), and WO 87/07607.

The amine of formula 111, wherein R$_2$ is hydrogen, can be prepared from a ketone of the formula

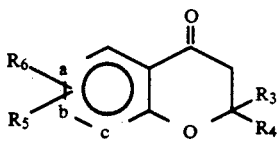

by standard methodology. The ketone of formula V can be obtained by literature procedures, such as disclosed by P. Sebok and T. Timar, *Heterocycles,* 1988, 27, 2595; P. Teixidor et al., *Heterocycles,* 1988, 27, 2459; A. Benerji and N. C. Goomer, *Tetrahedron Letters,* 1979, 3685; G. Ariamala and K. K. Subramanian, *Tetrahedron Letters,* Vol. 29, No. 28, p. 3487–3488 (1988).

The compounds of formula I wherein $R_1$ is

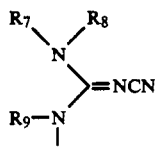

can also be prepared by heating a thiourea of the formula

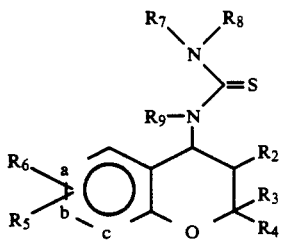

with monosodium cyanamide in the presence a carbodiimide such as 1-(3-dimethylaminopropyl)-3-ethylcarbodiimide or dicyclohexylcarbodiimide in an organic solvent.

The compounds of formula VI can be prepared from the amino alcohol of formula III by standard methods (i.e., the Rasmussen and Mozolis references above).

The compounds of formula I wherein $R_1$ is

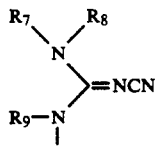

can also be prepared by reacting a compound of the formula

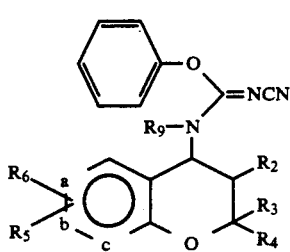

with an amine of the formula $$R_7R_8NH \qquad \text{VIII}$$

in a polar solvent such as isopropanol. The compounds of formula VII are prepared by reacting an amine of formula III with diphenylcyanocarbonimidate.

The compounds of formula I wherein R is

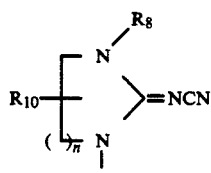

can be prepared by treating a compound of the formula

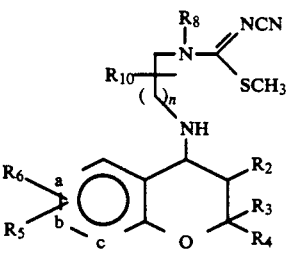

with mercuric acetate in an alcoholic solvent such as methanol.

The compounds of formula IX are prepared by treating a diamine of the formula

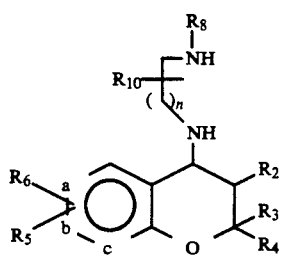

with dimethyl-N-cyanodithioiminocarbonate.

The compounds of formula I wherein $R_1$ is

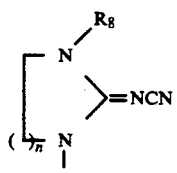

can also be prepared by treating a diamine of formula X with diphenylcyanocarbonimidate in an alcoholic solvent, such as 2-propanol.

The compound of formula X wherein $R_2$ is trans hydroxyl is obtained by treatment of an epoxide

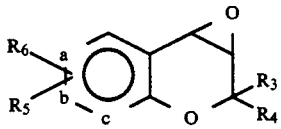

with diamine of the formula

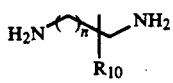

in an alcoholic solvent, such as ethanol.

The preparation of the epoxide XI is described by Evans and Lang (references above).

Compounds of formula X can also be prepared from the amino alcohol III and an alkylating agent of the formula

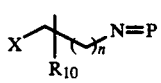

wherein P is a protecting group and X is a leaving group, such as Cl, Br and I, in the presence of a base catalyst, followed by deprotection. Compounds of formula X can also be prepared from a ketone or aldehyde of formula XIII (i.e., wherein X is oxo) and amino alcohol III by standard techniques of reductive amination followed by removal of the protection group P.

The compounds of the present invention wherein $R_2$ is OCOalkyl can be prepared by acylation of the alcohol of formula I, wherein $R_2$ is OH, with an acid chloride of the formula

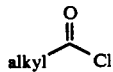

in the presence of a base catalyst, such as pyridine or triethylamine.

For the preparation of individual enantiomers of compounds of formula I (wherein $R_2$=H, OH), compound III ($R_2$=H, OH) is converted to diastereomeric amides of the formula

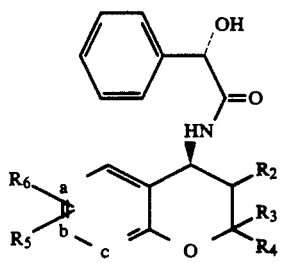

and

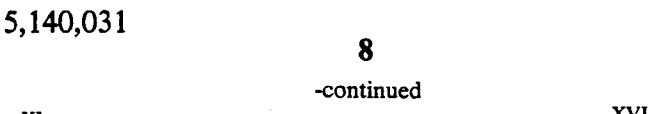

by treatment with chiral nonracemic mandelic acid in the presence of dicyclohexylcarbodiimide.

Compounds XV and XVI are separated by crystallization or chromatography. The enantiomer of mandelic acid that yields crystalline diastereomer with the desired 4R-stereochemistry of benzopyran (as shown in formula XV) is preferred in the resolution step.

Compounds XV and XVI are then hydrolyzed by heating in the presence of sulfuric acid in dioxane to give enantiomers of the formula

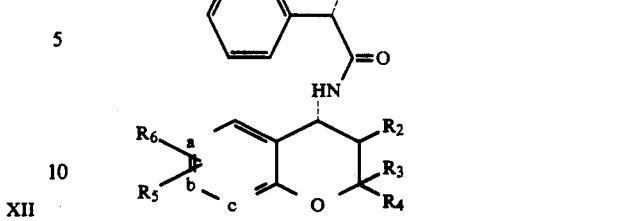

The enantiomers XVII and XVIII are then converted to chiral nonracemic compounds of formula I.

The compounds of the present invention can have asymmetric centers at carbons 2–4 of benzopyran ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractioanl crystallization methods.

The compounds of the present invention wherein $R_9$ and/or $R_8$ is hydrogen, can exist as a mixture of tautomers represented by the following structures. The tautomeric products are obtained in relative amounts that differ from compound to compound. All forms are included in the scope of formula I.

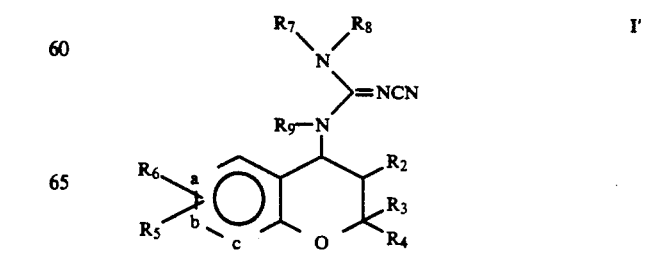

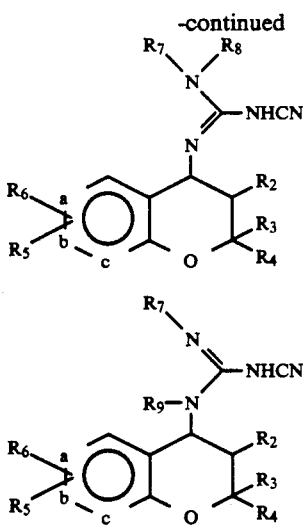

The compounds of formula I and the pharmaceutically acceptable salts act as potassium channel activators. Thus, compounds of the present invention are useful as anti-arrhythmic agents, antiischemic agents and in the treatment of hypertension.

It has been found that compounds of formula I wherein $R_7$ is aryl, arylalkyl, cycloalkyl, (cycloalkyl)alkyl, heterocyclo or (heterocyclo)alkyl are preferred as antiischemic agents, i.e., for the treatment of ischemic conditions such as myocardial ischemia, cerebral ischemia, lower limb ischemia and the like. Especially preferred are those compounds where $R_7$ is aryl or substituted aryl, i.e., substituted phenyl, and $R_8$ and $R_9$ are each hydrogen. While any of the compounds of formula I may be used as antiischemic agents, these preferred antiischemic agents have been found to possess little or no vasodilator activity. This means that in the treatment of ischemic heart, these compounds are less likely to cause coronary underperfusion. By "little or no vasodilator activity" is meant that these compounds have $IC_{50}$ (rat aorta) values greater than that of the known potassium channel activator, cromakalim. Preferred compounds for ischemia have $IC_{50}$ (methoxamine contracted rat aorta) values greater than that of cromakalim, especially >10 times that of cromakalim (i.e., have 1/10 the vasodilatory action of cromakalim) and most preferred are those compounds having $IC_{50}$ (rat aorta) values >50 times that of cromakalim.

Similarly, the most preferred compounds of formula I for reducing hypertension are those wherein $R_7$ is hydrogen or alkyl of 1 to 3 carbons, $R_7$ and $R_8$ taken together with the nitrogen atom to which they are attached for a 5- or 6-membered ring, such as pyrrolidine or piperidene, $R_9$ and $R_{10}$ are each hydrogen and n is 1 or 2.

Thus, for example, by the administration of a composition containing one (or a combination) of the compounds of this invention, ischemic conditions of a mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular (e.g., hypertension) and non-cardiovascular uses.

As a result of the potassium channel activating activity of compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, as well as for the promotion of hair growth (e.g., in the treatment of male pattern baldness) and as anti-asthmatic agents.

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Preferred are those compounds wherein
a is nitrogen or —$CR_5$;
b and c are each —$CH_{13}$;
$R_2$ is trans-hydroxy;
$R_3$ and $R_4$ are each methyl;
$R_5$ is —CN or —$NO_2$;
$R_6$ is hydrogen;
$R_7$ is phenyl or substituted phenyl;
$R_8$ is hydrogen;

R$_9$ is hydrogen;
R$_{10}$ is hydrogen; and
n is 1 or 2.

The most preferred compounds of the present invention, which are preferably employed as antiischemic agents, are where R$_7$ is phenyl or substituted phenyl.

Specific embodiments of the present invention are described hereinafter in the following examples.

EXAMPLE 1

(trans)N''-Cyano-N-(6-cyano-3,4-dihydro-3-hydroxy2,2-dimethyl-2H-1-benzopyran-4-yl)-N'-(1,1-dimethylpropyl)guanidine

A. N-Cyano-N'-(1,1-dimethylpropyl)thiourea

To a suspension of monosodium cyanamide (0.64 g, 10 mmol) in absolute ethanol (30 mL), 1,1-dimethylpropylisothiocyanate (1.29 g, 10 mmol) was added slowly at room temperature. Exothermic reaction occurred during addition and near the end of the addition, the initially heterogeneous mixture became a homogeneous solution. It was allowed to stir at room temperature for 2 hours and then heated at 75° C. for 1 hour. The reaction mixture was cooled to room temperature and the solid was filtered. The filtrate solution was concentrated to yield the title A compound (1.6 g) as a colorless solid.

B. (trans)-N''-Cyano-N-(6-cyano-3,4-dihydro-3-hydroxy-2,2-dimethyl-2H-1-benzopyran-4-yl)-N'-(1,1-dimethylpropyl)guanidine To a solution of the title A compound (0.94 g, 5.5 mmol) and (trans)-4-amino-3,4-dihydro-3-hydroxy-2,2-dimethyl-2H-1-benzopyran-6-carbonitrile (prepared according to Evans et al., *J. Med. Chem.*, 1983, 26, 1582 and *J. Med. Chem.*, 1986, 29, 2194) (1.0 g, 4.6 mmol) in dimethylformamide (5 mL) under argon, 1-(3-dimethylaminopropyl)-2-ethylcarbodiimide hydrochloride (1.14 g, 5.9 mmol) was added at room temperature. The reaction mixture was stirred at room temperature for 2 hours and then partitioned between 1N HCl and ethyl acetate. The organic layer was separated and the aqueous phase was reextracted with ethyl acetate and the combined organic phase was washed with water, aqueous sodium bicarbonate and brine. After drying over anhydrous magnesium sulfate, the filtrate was concentrated and the residue was purified by flash chromatography on silica gel (1:1 Hexane/EtOAc). The fractions containing the desired product were combined and concentrated to yield a colorless solid (620 mg). This solid was triturated with isopropyl ether to yield the title compound, m.p. 207°-208° C.

Analysis calc'd for C$_{19}$H$_{25}$N$_5$O$_2$:
C, 64.20; H, 7.09; N, 19.71;
Found: C, 64.04; H, 7.11; N, 19.44.

EXAMPLE 2

(trans)-N''-Cyano-N-(6-cyano-3,4-dihydro-3-hydroxy2,2-dimethyl-2H-1-benzopyran-4-yl)-N'-ethyl guanidine

A. N-Cyano-N'-ethylthiourea

To a suspension of monosodium cyanamide (6.4 g, 100 mmol) in absolute ethanol (30 mL), ethylisothiocyanate (9.0 mL, 100 mmol) was added slowly with stirring at room temperature. During addition, exothermic reaction occurred and near the end of the addition the reaction mixture became a homogeneous solution. It was allowed to stir at room temperature for 2 hours and then heated at 75° C. for 1 hour. The reaction mixture was cooled to room temperature and the insoluble material was filtered off (700 mg). The mother liquor was concentrated and the resulting solid was triturated with isopropanol-isopropyl ether to yield the title A compound (11.2 g), m.p. >240° C.

B. (trans)-N''-Cyano-N-(6-cyano-3,4-dihydro-3-hydroxy-2,2-dimethyl-2H-1-benzopyran-4-yl)-N'-ethyl guanidine To a solution of the title A compound (1.15 g, 8.9 mmol) and (trans)-4-amino-3,4-dihydro-3-hydroxy-2,2-dimethyl-2H-1-benzopyran-6-carbonitrile (prepared according to Evans et al., *J. Med. Chem.*, 1983, 26, 1582 and *J. Med. Chem.*, 1986, 29, 2194). (1.5 g, 6.9 mmol) in dimethylformamide (5 mL) under argon was added 1-(3-dimethylaminopropyl)-2-ethylcarbodiimide hydrochloride (1.71 g, 8.9 mmol) at room temperature. The reaction mixture was stirred at room temperature for 2 hours and then partitioned between 1N HCl and ethyl acetate. The organic phase was separated and the aqueous phase was reextracted with ethyl acetate. The combined organic phase was washed with water, aqueous sodium bicarbonate and brine. After drying over anhydrous magnesium sulfate, the solvent was evaporated and the residue was purified by flash chromatography on silica gel (25% acetone in dichloromethane). The fractions containing the desired product were combined and evaporated to yield a colorless solid (801 mg). This solid product was recrystallized from acetonitrile-ether to yield the title compound, m.p. 185°-188° C.

Analysis calc'd for C$_{16}$H$_{19}$N$_5$O$_2$ 0.2 H$_2$O:
C, 60.64; H, 6.17; N, 22.10;
Found: C, 60,63; H, 6.16; N, 22.25.

EXAMPLE 3

(trans)-N''-Cyano-N-(6-cyano-3,4-dihydro-3-hydroxy-2,2-dimethyl-2H-1-benzopyran-4-yl)-N'-phenyl guanidine

A. N-cyano-N'-phenylthiourea

To a suspension of monosodium cyanamide (6.4 g, 100 mmol) in absolute ethanol (170 mL), phenylisothiocyanate (12.5 mL, 104.5 mmol) was added slowly with stirring at room temperature. The reaction was allowed to stir at room temperature for 1 hour and then heated at 75° C. for 4 hours. The reaction was cooled to room temperature and the colorless solid was filtered and washed with ethanol to give the title A compound (13.6 g), m.p. >250° C.

B.
(trans)-N″-Cyano-N-(6-cyano-3,4-dihydro-3-hydroxy-2,2-dimethyl-2H-1-benzopyran-4-yl)-N′-phenyl guanidine To a solution of the title A compound (1.06 g, 5.96 mmol) and (trans)-4-amino-3,4-dihydro-3-hydroxy-2,2-dimethyl-2H-1-benzopyran-6-carbonitrile (prepared according to Evans et al., *J. Med. Chem.*, 1983, 26, 1582 and *J. Med. Chem.*, 1986, 29, 2194). (1.0 g, 4.59 mmol) in dimethylformamide (5 mL) under argon, 1-(3-dimethylaminopropyl)-2-ethylcarbodiimide hydrochloride (1.17 g, 5.96 mmol) was added at room temperature. The reaction mixture was stirred at room temperature for 2 hours and then partitioned between 1N HCl and ethyl acetate. The organic phase was separated and the aqueous phase was reextracted with ethyl acetate and the combined organic phase was washed with water, aqueous sodium bicarbonate and brine. After drying over anhydrous magnesium sulfate, the solvent was evaporated and the colorless residue was triturated with ether to yield the title compound (1.3 g), m.p 247°–249° C. (with effervescence).

Analysis calc'd for $C_{20}H_{19}N_5O_2$:
C, 66.46; H, 5.30; N, 19.38;
Found: C, 66.09; H, 5.30; N, 19.35.

EXAMPLE 4
(trans)-N′-Cyano-N-(3,4-dihydroxy-3-hydroxy-2,2-dimethyl-6-nitro-2H-1-benzopyran-4-yl)-N′-ethylguanidine To a solution of the title A compound from Example 2 (1.2 g, 9.4 mmol) and (trans)-4-amino-3,4-dihydro-2,2-dimethyl-6-nitro-2H-1-benzopyran (1.5 g, 6.3 mmol) (prepared according to Evans et al., *J. Med. Chem.*, 1983, 26, 1582 and *J. Med. Chem.*, 1986, 29, 2194) in dimethylformamide (5 ml) under argon, 1-(3-dimethylaminopropyl)-2-ethylcarbodiimide hydrochloride (2.1 g, 10.7 mmol) was added at room temperature. The reaction mixture was stirred at room temperature for 2 hours and then partitioned between 1N HCl and ethyl acetate. The organic phase was taken and the aqueous phase was reextracted with ethyl acetate and the combined organic phase was washed with water, aqueous sodium bicarbonate and brine. After drying over anhydrous magnesium sulfate, the solvent was evaporated and the residue was purified by flash chromatography on silica gel (Hexane/Acetone/6:4) to yield a colorless solid (500 mg). This was triturated with isopropyl ether to provide the title compound, m.p. 204°–205° C.

Analysis calc'd for $C_{15}H_{19}N_5O_4 \cdot 0.17H_2O$:
C, 53.55; H, 5.79; N, 20.82;
Found: C, 53.89; H, 5.63; N, 20.48.

EXAMPLE 5
(trans)-3,4-Dihydro-3-hydroxy-2,2-dimethyl-4-[2-(cyanoimino)-1-pyrrolidinyl]-2H-1-benzopyran-6-carbonitrile

A.
(trans)-4-[(2-Aminoethyl)amino]-3,4-dihydro-3-hydroxy-2,2-dimethyl-2H-1-benzopyran-6-carbonitrile To a suspension of 6-cyano-3,4-epoxy-3,4-dihydro-2,2-dimethyl-2H-benzopyran (1.2 g, 5.97 mmol) (prepared according to Evans et al., *J. Med. Chem.*, 1983, 26, 1582 and *J. Med. Chem.*, 1986, 29, 2194) in ethanol (7.0 mL), ethylenediamine (2.4 mL, 35.8 mmol) was added at room temperature and the reaction mixture was stirred at room temperature for 36 hours. The solvent was removed under reduced pressure and the residue was further dried by use of vacuum pump to yield the title A compound (1.74 g, >100%) as a colorless foam. This material was used for the next reaction without any purification.

B.
(trans)-3,4-Dihydro-3-hydroxy-2,2-dimethyl-4-[2-(cyanoimino)-1-pyrrolidinyl]-2H-1-benzopyran-6-carbonitrile To a solution of the title A compound (1.74 g, 5.97 mmol) in ethanol at room temperature, triethylamine (1.7 mL, 11.94 mmol) was added slowly, followed by dimethyl N-cyanodithioiminocarbonate (1.16 g, 11.94 mmol of 90%). The reaction mixture was heated at 80° C. for 3 hours and then cooled to ambient temperature. The solvent was evaporated to give a light yellow foam (2.4 g). This material was taken up in methanol (20 mL) and the resulting suspension was treated with mercuric acetate (2.52 g, 7.77 mmol). The reaction mixture was stirred at room temperature for 2 hours and the solvent was evaporated under reduced pressure. The residue was diluted with water, alkalized to pH~9.0 with 5N NaOH and the product was extracted with 5% methanolic chloroform. The combined organic extracts were washed with brine whereby a thick emulsion resulted. The two phase mixture was filtered through a celite pad and the organic layer was separated and dried over magnesium sulfate. The solvent was evaporated and the residue was purified by flash chromatography (5% methanol in chloroform) on silica gel to provide a colorless residue. This residue was triturated with ethyl acetate to yield the desired product (740 mg). The mother liquour was concentrated and triturated with ethyl acetate to provide a second crop (370 mg) for a total of 1.1 g. The combined material was recrystallized from hot ethyl accetate to give the title compound as a white powder, m.p. 254°–255° C.

Analysis calc'd for $C_{16}H_{17}N_5O_2 \cdot 0.42 H_2O$:
C, 60.27; H, 5.63; N, 21.97;
Found: C, 60.40; H, 5.30; N, 21.84.

EXAMPLE 6
(trans)-N″-Cyano-N-(3,4-dihydro-3-hydroxy-2,2-dimethyl-2H-pyrano[3,2-c]pyridin-4-yl)phenylguanidine To a solution of the title A compound from Example 3 (2.2 g, 12.5 mmol) and (trans)-4-amino-3,4-dihydro-2,2-dimethyl-2H-pyrano[3,2-c]pyridin-3-ol (1.1 g, 5.7 mmol) (prepared according to EP 0 205 292 A2) in dimethylformamide (5 ml) under argon, 1-(3-dimethylaminopropyl)-2-ethylcarbodiimide hydrochloride (2.2 g, 10.8 mmol) was added at room temperature. The reaction mixture was stirred at room temperature for 2 hours and then partitioned between water (pH ~11) and ethyl acetate. The organic phase was separated and the aqueous phase was reextracted with ethyl acetate and the combined organic phase was washed with water, aqueous sodium bicarbonate and brine. After drying over anhydrous magnesium sulfate, the solvent was evaporated and the residue was purified by flash chromatography on silica gel (acetone:dichloromethane/1:4) to yield a colorless solid (470 mg) which was crystallized from acetonitrile to provide the title compound, m.p. 233°–236° C.

Analysis calc'd for $C_{18}H_{19}N_5O_2$:

C, 64.08; H, 5.67; N, 20.76;
Found: C, 63.88; H, 5.48; N, 20.76.

EXAMPLE 7

(trans)-N'-Cyano-N-(6-cyano-3,4-dihydro-3-hydroxy-2,2-dimethyl-2H-1-benzopyran-4-yl)-1-pyrrolidinecarboximidamide

A.
(trans)-4-[[(Cyanoimino)phenoxymethyl]amino]-3,4-dihydro-3-hydroxy-2,2-dimethyl-2H-1-benzopyran-6-carbonitrile To a solution of (trans)-4-amino-3,4-dihydro-3-hydroxy-2,2-dimethyl-2H-1-benzopyran-6-carbonitrile (prepared according to Evans et al., *J. Med. Chem.*, 1983, 26, 1582 and *J. Med. Chem.*, 1986, 29, 2194) (5.0 g, 23 mmol) in isopropanol (50 mL), diphenylcyanocarbonimidate (5.5 g, 25 mmol) was added at room temperature and the reaction mixture was allowed to stir at room temperature for 16 hours. Most of the isopropanol was evaporated and the residue was dissolved in ethyl acetate. The resulting solution was washed successively with 10% citric acid, 1N sodium hydroxide solution and brine. It was dried over anhydrous magnesium sulfate, concentrated and the residue was crystallized from chloroform-isopropyl ether to yield the title A compound (4.2 g) as a colorless solid, m.p. 186°-188° C.

Analysis calc'd for $C_{20}H_{18}N_4O_3 \cdot 0.6H_2O$:
C. 64.37; H, 5.18; N, 15.02;
Found: C, 64.64; H, 4.86; N, 14.75.

B
(trans)-N'-Cyano-N-(6-cyano-3,4-dihydro-3-hydroxy-2,2-dimethyl-2H-1-benzopyran-4-yl)-1-pyrrolidine-carboximidamide To a solution of title A compound (0.8 g, 12.2 mmol) in isopropanol (4 mL), pyrrolidine (0.5 mL) was added at room temperature and the reaction mixture was allowed to stir at room temperature overnight. The suspension was diluted with ether and the colorless solid was filtered and dried to yield the title compound (0.4 g), m.p. 263°-264° C.

Analysis calc'd for $C_{18}H_{21}N_5O_2$:
C, 63.70; H, 6.24; N, 20.64;
Found: C, 63.45; H, 6.29; N, 20.88.

EXAMPLE 8

(trans)-N''-Cyano-N-(6-cyano-3,4-dihydro-3-hydroxy-2,2-dimethyl-2H-1-benzopyran-4-yl)-N'-ethyl-N-methylguanidine

A.
(trans)-N'-Cyano-N-(6-cyano-3,4-dihydro-3-hydroxy-2,2-dimethyl-2H-1-benzopyran-4-yl)-N-methylcarbamidic acid, phenyl ester To a solution of (trans)-3,4-dihydro-3-hydroxy-2,2-dimethyl-4-(methylamino)-2H-1-benzopyran-6-carbonitrile (prepared according to Evans et al., *J. Med. Chem.*, 1983, 26, 1582 and *J. Med. Chem.*, 1986, 29, 2194) (1.0 g, 4.3 mmol) in isopropanol (4 mL), diphenylcyanocarbonimidate (1.0 g, 4.3 mmol) was added at room temperature and the reaction mixture was allowed to stir at room temperature for 16 hours. Most of the isopropanol was evaporated and the residue was dissolved in ethyl acetate. The resulting solution was washed successively with 10% citric acid, 1N sodium hydroxide and brine. It was dried over anhydrous magnesium sulfate and concentrated. The resiude was purified by flash chromatography (ethyl acetate:hexanes 1:1) on silica gel to yield the title A compound. This compound was used for the next step without further purification.

B.
(trans)-N''-Cyano-N-(6-cyano-3,4-dihydro-3-hydroxy-2,2-dimethyl-2H-1-benzopyran-4-yl)-N'-ethyl-N-methylguanidine To a solution of the title A compound (0.1 g, 0.27 mmol) in isopropanol (1 mL) and triethyl amine (0.25 mL), ethyl amine hydrochloride (0.1 g, 1.2 mmol) was added at room temperature and the reaction mixture was allowed to stir at room temperature overnight. Most of the solvent was evaporated and the residue was dissolved in ethyl acetate. The solution was washed successively with 10% citric acid, aqueous sodium bicarbonate and brine. After drying over anhydrous magnesium sulfate, the solvent was evaporated and the residue was triturated with ether to yield the title compound as a colorless solid, m.p. 227°-228° C.

EXAMPLE 9

(trans)-N''-Cyano-N-(6-cyano-3,4-dihydro-3-hydroxy-2,2-dimethyl-2H-1-benzopyran-4-yl)-N'-[2(dimethylamino)ethyl]guanidine To a suspension of the compound from Example 7, part A (0.8 g, 2.2 mmol) in isopropanol (3 ml), 95% 1,1-dimethylethylenediamine (0.5 g, 5.7 mmol) was added at room temperature. It was allowed to stir at room temperature for 20 hours and concentrated in vacuo. The residue was triturated with isopropyl ether to give the title compound (0.4 g) as a white solid, m.p. 172°-173° C.: $^1$H NMR (CDCl$_3$) δ 7.6 (s, 1 H), 7.4 (dd, J=2.0 & 9.0 Hz, 1H), 6.9 (d, J=9.0 Hz, 1 H), 6.6 (s, 1 H), 4.9 (t, J=9.0 Hz, 2 H), 3.5 (d, J=9.0 Hz, 1 H), 3.4 (s, 2 H), 2.5 (m, 2 H), 2.0 (s, 6 H), 1.5 (s, 3 H), 1.3 (s, 3 H); $^{13}$C NMR (CDCl$_3$) δ 163.4, 156.8, 133.1, 132.5, 122.8, 118.8, 118.7, 118.0, 103.9, 80.4, 76.2, 69.1, 60.8, 51.8, 44.6, 41.7, 26.4, 18.5; IR (KBr) 1126.9, 1267.0, 1431.4, 1489.0, 1577.0, 1635.8, 2173.3, 3391.9, 3407.6 cm$^{-1}$.

Analysis calc'd for $C_{18}H_{24}N_6O_2$:
C, 60.65; H, 6.79; N, 23.58;
Found: C, 60.53; H, 6.75; N, 23.62.

EXAMPLE 10

(trans)-N''-Cyano-N-(6-cyano-3,4-dihydro-3-hydroxy-2,2-dimethyl-2H-1-benzopyran-4-yl)-N'-methylguanidine To a suspension of the compound of Example 7, part A (1.0 g, 2.8 mmol) in isopropanol (6 ml), methylamine (40% solution in methanol, 1 ml) was added at room temperature. The reaction mixture was allowed to stir at room temperature for 20 hours and concentrated in vacuo. The crude product obtained was crystallized from isopropanol to give the title compound (0.4 g) as a white solid, m.p. 212°-214° C.: $^1$H NMR (CDCl$_3$/DMSO) δ 7.5 (s, 1 H), 7.45 (d, J=9.0 Hz, 1 H), 6.9 (m, 2 H), 6.8 (d, J=8.0 Hz, 1 H), 5.55 (br, 1 H), 4.85 (br, 1 H), 3.7 (m, 1 H), 2.88 (d, J=5.0 Hz, 3 H), 1.48 (s, 3 H), 1.24 (s, 3 H); $^{13}$C NMR (CDCl$_3$/DMSO) 160.5, 155.5, 131.6, 131.3, 123.7, 117.9, 117.3, 116.9, 102.2, 79.4, 76.6, 70.9, 27.6, 25.6, 17.7; IR (KBr) 1267, 1419, 1489, 1576, 1608, 2170, 2225, 2977, 3338 cm$^{-1}$.

Analysis calc'd for $C_{15}H_{17}N_5O_2 \cdot 0.3 H_2O$:
C, 59.16; H, 5.82; N, 23.01;
Found: C, 59.16; H, 5.57; N, 23.01.

EXAMPLE 11

(trans)-4-[(Cyanoimino)[[4-(phenylmethyl)-1-piperazinyl]methyl]amino]-3,4-dihydro-3-hydroxy-2,2-dimethyl-2H-1-benzopyran-6-carbonitrile To a suspension of the compound from Example 7, part A (2.0 g, 5.5 mmol) in isopropanol (5 ml), 4-(phenylmethyl)-1-piperazine (1.0 ml) was added at room temperature. The reaction mixture was allowed to stir at room temperature for 20 hours and concentrated in vacuo. The crude product obtained was purified by flash chromatography on silica gel eluting with dichloromethane/acetone (7/3) to give the title compound (0.6 g). It was recrystallized from isopropanol-ether to give the desired product (250 mg) as a white solid, m.p. 205°-207° C.: $^1$H NMR (DMSO-d$_6$) δ 7.4 (s, 1 H), 7.3 (d, J=8.0 Hz, 1 H), 7.2 (d, J=8.0 Hz, 1 H), 7.0 (s, 6 H), 6.6 (d, J=9.0 Hz, 1 H), 5.6 (d, J=6.0 Hz, 1 H), 4.6 (t, J=8.0 & 10.0 Hz, 1 H), 3.2 (m, 5 H), 2.2 (m, 5 H), 1.14 (s, 3 H), 0.88 (s, 3 H); $^{13}$C NMR (DMSO-d$_6$) 161.1, 156.4, 137.6, 133.1, 132.9, 129,1, 128.3, 127.2, 124.6, 117.9, 102.7, 80.6, 71.5, 61.9, 53.0, 52.2, 46.6, 26.7, 18.6; IR (KBr) 1125, 1490, 1524, 1577, 1611, 2170, 2224, 3429 cm$^{-1}$.

Analysis calc'd for C$_{25}$H$_{28}$N$_6$O$_2$:
  C, 67.54; H, 6.35; N, 18.91;
Found: C, 67.29; H, 6.37; N, 18.73.

EXAMPLE 12

(trans)-N"-Cyano-N-(6-cyano-3,4-dihydro-3-hydroxy-2,2-dimethyl-2H-1-benzopyran-4-yl)guanidine To a suspension of the compound of Example 7, part A (1.0 g, 2.8 mmol) in isopropanol (6 ml), ammonium hydroxide (1 ml) was added at room temperature. It was allowed to stir at room temperature for 20 hours and concentrated in vacuo. The crude product obtained was crystallized from acetone/ethyl acetate to give the title compound (0.31 g) as a white solid, m.p. 250°-251° C.: $^1$H NMR (DMSO-d$_6$) δ 7.7 (dd, J=2.0 & 7.0 Hz, 1 H), 7.5 (s, 1 H), 6.9 (m, 2 H), 7.0 (d, J=9.0 Hz, 1 H), 5.8 (br s, 1 H), 4.8 (br s, 1 H), 3.6 (m, 1 H), 1.48 (s, 3 H), 1.25 (s, 3 H); $^{13}$C NMR (DMSO-d$_6$) 162.3, 156.3, 132.9, 132.6, 124.8, 119.1, 118.1, 102.7, 80.5, 71.3, 26.5, 19.0; IR (KBr) 1064, 1268, 1489.7, 1555, 1635, 2183, 2225, 3432 cm$^{-1}$.

Analysis calc'd for C$_{14}$H$_{15}$N$_5$O$_2$:
  C, 58.93; H, 5.30; N, 24.55;
Found: C, 58.74; H, 5.32; N, 24.23.

EXAMPLE 13

(trans)-N"-Cyano-N-(6-cyano-3,4-dihydro-3-hydroxy-2,2-dimethyl-2H-1-benzopyran-4-yl)-N'-(methylethyl)-guanidine To a suspension of the compound from Example 7, part A (2.0 g, 5.5 mmol) in isopropanol (5 ml), isopropylamine (1.5 ml) was added at room temperature. It was allowed to stir at room temperature for 20 hours and concentrated in vacuo. The crude product obtained was purified by flash chromatography on silica gel eluting with 7/3 dichloromethane/acetone to give the title compound (1.2 g). This solid was crystallized from isopropanol-isopropyl ether to give the desired product as a white solid, m.p. 150°-152° C.: $^1$H NMR (DMSO-d$_6$) δ 7.6 (dd, J=2.0 & 7.0 Hz, 1 H), 7.5 (s, 1 H), 7.2 (d, J=9.0 Hz, 1 H), 7.0 (d, J=9.0 Hz, 1 H), 6.8 (d, J=8.0 Hz, 1 H), 5.9 (d, J=5.0 Hz, 1 H), 4.8 (t, J=9.0 Hz, 1 H), 3.9 (m, 1 H), 3.8 (m, 1 H), 1.47 (s, 3 H), 1.24 (s, 3 H), 1.2 (d, J=3.0 Hz, 6 H); $^{13}$C NMR (DMSO-d$_6$) 159.5, 156.3, 132.7, 132.4, 125.2, 119.1, 118.0, 117.8, 102.7, 80.5, 71.1, 51.5, 43.4, 26.7, 22.6, 22.4, 18.7; IR (KBr) 1268, 1490, 1587.8, 2170, 2226, 2978, 3419 cm$^{-1}$.

Analysis calc'd for C$_{17}$H$_{21}$N$_5$O$_2$.0.1 H$_2$O:
  C, 62.03; H, 6.49; N, 21.28;
Found: C, 61.75; H, 6.66; N, 21.86.

EXAMPLE 14

(trans)-N"-Cyano-N-(6-cyano-3,4-dihydro-3-hydroxy-2,2-dimethyl-2H-1-benzopyran-4-yl)-N'-dimethylguanidine To a suspension of the compound from Example 7, part A (1.0 g, 2.8 mmol) in isopropanol (6 ml), dimethylamine hydrochloride (0.33 g, 4.2 mmol) was added, followed by powdered potassium carbonate (0.57 g, 4.2 mmol) at room temperature. The reaction mixture was allowed to stir at room temperature for 20 hours and concentrated in vacuo. The residue was dissolved in chloroform (150 ml) and washed with water, dried over magnesium sulfate and concentrated in vacuo. The crude product obtained was crystallized from dichloromethane-ether to give the title compound (0.44 g) as a white solid. This solid was recrystallized from acetonitrile-chloroform to give colorless solid, m.p. 196°-197° C. $^1$H NMR (DMSO-d$_6$) 6 7.7 (s, 1 H), 7.6 (dd, J=3.0 & 8.0 Hz, 1 H), 7.2 (d, J=9.0 Hz, 1 H), 6.9 (d, J=9.0 Hz, 1 H), 5.8 (d, J=6.0 Hz, 1 H), 4.9 (t, J=9.0 & 10.0 Hz, 1 H), 3.6 (dd, J=8.0 & 5.0 Hz, 1 H), 3.0 (s, 6 H), 1.42 (s, 3 H), 1.24 (s, 3 H); $^{13}$C 1 NMR (DMSO-d$_6$) 159.3, 154.9, 131.5, 130.8, 123.4, 116.1, 101.4, 78.9, 70.3, 51.5, 25.2, 17.0; IR (KBr) 1143, 1269, 1398, 1489, 1527, 1595, 2168, 2226, 2935, 2980, 3433 cm$^{-1}$.

Analysis calc'd for C$_{16}$H$_{19}$N$_5$O$_2$.0.5 H$_2$O:
  C, 59.61; H, 6.25; N. 21.73;
Found: C, 59.44; H, 5.95; N, 22.03.

EXAMPLE 15

(trans)-N"-Cyano-N-(6-cyano-3,4-dihydro-3-hydroxy-2,2-dimethyl-2H-1-benzopyran-4-yl)-N'-phenylmethylguanidine To a suspension of the compound from Example 7, part A (0.5 g, 1.4 mmol) in isopropanol (3 ml) was added benzylamine (90% 0.5 ml) at room temperature. The reaction mixture was allowed to stir at room temperature for 20 hours and concentrated in vacuo. The residue was combined with another batch of the same material and purified by flash chromatography on silica gel eluting with hexaneethyl acetate (3:7) to give a white solid (0.8 g). This solid was crystallized from acetonitrileisopropyl ether to give the title compound as a colorless solid, m.p. 188°-189° C.: $^1$H NMR (CDCl$_3$) δ 7.7 (m, 1 H), 7.5 (dd, J=2.0 & 9.0 Hz, 1 H), 7.4 (m, 6 H), 6.86 (d, J=9.0 Hz, 1 H), 5.8 (s, 1 H), 4.8 (m, 1 H), 4.5 (d, J=5.0 Hz, 2 H), 3.7 (dd, J=6.0 & 4.0 Hz, 1 H), 1.41 (s, 3 H), 1.19 (s, 3 H); $^{13}$C NMR (CDCl$_3$) 158.7, 154.5, 136.8, 130.7, 126.5, 125.2, 125.0, 123.0, 116.0, 101.0, 78.6, 42.6, 16.9; IR (KBr) 1267, 1491, 1579, 1595, 2175, 2222, 3433 cm$^{-1}$.

Analysis calc'd for C$_{21}$H$_{21}$N$_5$O$_2$:
  C, 67.18; H, 5.64; N, 18.66;
Found: C, 67.14; H, 5.55; N, 18.65.

EXAMPLE 16

(trans)-N''-Cyano-N-(6-cyano-3,4-dihydro-3-hydroxy-2,2-dimethyl-2H-1-benzopyran-4-yl)-N'-[2-[(phenylmethyl)methylamino]ethyl]guanidine To a suspension of the compound from Example 7, part A (0.5 g, 1.4 mmol) in isopropanol (3 ml), N-methylbenzylethylamine (0.5 ml) was added at room temperature. The reaction mixture was allowed to stir at room temperature for 24 hours. The initially heterogeneous mixture became a homogeneous solution slowly and as the reaction proceeded the product precipitated out of the reaction mixture. Upon completion of reaction, the solid was filtered and triturated with ether to give the title compound (0.45 g) as a colorless solid, m.p. 184°–185° C.: $^1$H NMR (CDCl$_3$) δ 9.4 (s, 1 H), 7.59 (d, J=8.0 Hz, 1 H), 7.2 (m, 4 H), 6.96 (s, 2 H), 6.87 (d, J=9.0 Hz, 1 H), 6.4 (s, 1 H), 4.9 (m, 2 H), 3.4 (m, 4 H), 2.6 (m, 2 H), 2.1 (s, 3 H), 1.49 (S, 3 H), 1.26 (s, 3 H); $^{13}$C NMR (CDCl$_3$) 205.2, 160.7, 155.6, 131.6, 128.0, 127.4, 126.2, 123.5, 118.0, 117.3, 117.1, 102.4, 79.4, 61.3, 55.6, 40.5, 25.7, 17.74; IR (KBr) 1126, 1267, 1489, 1575, 1608, 2172, 2224, 2800, 2976, 3421 cm$^{-1}$.

Analysis calc'd for C$_{24}$H$_{28}$N$_6$O$_2$:
C, 66.64; H, 6.52; N, 19.43;
Found: C, 66.40; H, 6.52; N, 19.99.

EXAMPLE 17

(trans)-N''-Cyano-N-(6-cyano-3,4-dihydro-3-hydroxy-2,2-dimethyl-2H-1-benzopyran-4yl)-N'-(2-methoxyethyl)guanidine To a suspension of the compound from Example 7, part A (0.5 g, 1.4 mmol) in isopropanol (3 ml), 2-methoxyethylamine (0.12 g, 1.7 mmol, 0.15 ml) was added at room temperature. The reaction mixture was allowed to stir at room temperature for 20 hours and concentrated in vacuo. The residue was purified by flash chromatography on silica gel eluting with ethyl acetate to give the title compound (0.3 g) as a colorless solid, m.p. 94°–96° C.: $^1$H NMR (CDCl$_3$) δ 7.5 (s, 1 H), 7.38 (d, J=7.0 Hz, 1 H), 6.8 (m, 3 H), 4.86 (s, 1 H), 4.0 (m, 1 H), 3.5 (m, 4 H), 3.2 (s, 3 H), 1.9 (s, 1 H), 1.43 (s, 3 H), 1.19 (s, 3 H); $^{13}$C NMR (CDCl$_3$) 162.6, 156.8, 133.2, 132.4, 122.5, 119.0, 118.5, 118.1, 103.9, 80.2, 74.7, 60.3, 58.9, 52.2, 26.4, 21.0, 18.7, 14.1; IR (KBr) 1635, 1693, 3404 cm$^{-1}$.

Analysis calc'd for C$_{17}$H$_{21}$N$_5$O$_3$.0.24 H$_2$O:
C, 58.71; H, 6.23; N, 20.14;
Found: C, 58.81; H, 6.38; N, 20.04.

EXAMPLE 18

(3S-trans)-N''-Cyano-N-(6-cyano-3,4-dihydro-3-hydroxy-2,2-dimethyl-2H-1-benzopyran-4-yl)-N'phenylguanidine

A.

[3R-[3α,4β(S*)]]-N-(6-Cyano-3,4-dihydro-3-hydroxy-2,2-dimethyl-2H-1-benzopyran-4-yl)-α-hydroxybenzeneacetamide and

[3S-[3α,4β(R*)]]-N-(6-Cyano-3,4-dihydro-3-hydroxy-2,2-dimethyl-2H-1-benzopyran-4-yl)-α-hydroxybenzeneacetamide To a solution of (trans)-4-amino-3,4-dihydro-3-hydroxy-2,2-dimethyl-2H-1-benzopyran-6-carbonitrile (prepared according to Evans et al, *J. Med. Chem.*, 1983, 26, 1582 and *J. Med. Chem.*, 1986, 29, 2194) (10.0 g, 45.9 mmol), S-(+)-mandelic acid (6.98 g, 45.9 mmol), hydroxybenzotriazole hydrate (6.2 g, 45.9 mmol) in dimethylformamide (60 ml) at 0° C. was added dicyclohexylcarbodiimide (9.5 g, 45.9 mmol). It was allowed to stir at room temperature for 20 hours and then cooled in an ice bath. The precipitated solid was filtered and the filtrate was concentrated in vacuo. The residue was dissolved in 5 percent methanol in chloroform and washed with 1 N sodium hydroxide, 1 N hydrochloric acid, brine and dried over anhydrous magnesium sulfate. After removing drying agent, the solvent was removed in vacuo. The residue was crystallized from ethanol to give [3R-[3α,4β(S*)]]-N-(6-cyano-3,4-dihydro-3-hydroxy-2,2-dimethyl-2H-1-benzopyran-4-yl)-α-hydroxybenzeneacetamide (6.0 g) as a white solid, m.p. 238°–240° C., [α$_D$]$^{25}$= +94.6° (c=1, MeOH): $^1$H NMR (CDCl$_3$) δ 7.4 (m, 5 H), 7.26 (t, J=1.0 HZ, 1 H), 6.97 (d, J=9.0 HZ, 1 H), 6.83 (d, J=9.0 HZ, 1 H), 5.16 (s, 1 H), 4.98 (t, J=9.0 HZ, 1 H, 3.8 (d, J=5.0 HZ, 1 H), 3.55 (dd, J=4.0 & 5.0 HZ, 1 H), 1.45 (s, 3 H), 1.2 (s, 3 H).

Analysis calc'd for C$_{20}$H$_{20}$N$_2$O$_4$:
C, 68.17; H, 5.72; N, 7.95;
Found: C, 67.92; H, 5.49; N, 8.05.

The residual material of the mother liquor was purified by flash chromatography on silica gel eluting with hexane-ethyl acetate mixture (3:7) and the residue was crystallized from dichloromethaneisopropyl ether to give [3S-[3α,4β(R*)]]-N-(6-cyano-3,4-dihydro-3-hydroxy-2,2-dimethyl-2H-1-benzopyran-4-yl)-α-hydroxybenzeneacetamide (6.0 g) as a white solid, m.p. 100°–102° C. (foaming); [α$_D$]$^{25}$= −26.1° (c=1, MeOH): $^1$H NMR (DMSO-d$_6$) δ 8.45 (d, J=8.0 Hz, 1 H), 7.5 (m, 4 H), 7.3 (m, 2 H), 7.0 (s, 1 H), 6.88 (d, J=8.0 Hz, 1 H), 6.2 (s, 1 H), 5.57 (d, J=5.0 Hz, 1 H), 5.0 (s, 1 H), 4.76 (t, J=9.0 Hz, 1 H), 3.75 (dd, J=5.0 & 5.0 Hz, 1 H), 1.40 (S, 3 H), 1.15 (s, 3 H).

Analysis calc'd for C$_{20}$H$_{20}$N$_2$O$_4$.0.25 H$_2$O:
C, 67.30; H, 5.78; N, 7.84;
Found: C, 67.54; H, 5.95; N, 7.44.

B. (3S-trans)-4-Amino-3,4-dihydro-3-hydroxy-2,2-dimethyl-2H-1-benzopyran-6-carbonitrile To a solution of [3S-[3α,4β(R*)]]-N-(6-cyano-3,4-dihydro-3-hydroxy-2,2-dimethyl-2H-1-benzopyran-4-yl)-o-hydroxybenzeneacetamide, title A compound (2.8 g, 7.9 mmol) in dioxane (30 ml) was added a solution of sulfuric acid (2.5 g) in water (12 ml) at room temperature and the reaction mixture was heated at reflux temperature for 24 hours. It was concentrated in vacuo and the residue was dissolved in ethyl acetate (200 ml). The organic layer was washed with 1 N sodium hydroxide (50 ml) followed by water (50 ml) and dried over anhydrous magnesium sulfate and concentrated in vacuo to give the title B compound (1.6 g) as an oil: $^1$H NMR (CDCl$_3$) δ 7.74 (s, 1 H), 7.42 (dd, J=2.0 & 6.0 Hz, 1 H), 6.82 (d, J=8.0 Hz, 1 H), 3.65 (d, J=10.0 Hz, 1 H), 3.36 (d, J=10.0 Hz, 1 H), 1.53 (s, 3 H), 1.23 (s, 3 H).

C. (3S-trans)-N''-cyano-N-(6-cyano-3,4-dihydro-3-hydroxy-2,2-dimethyl-2H-1-benzopyran-4-yl)-N'-phenylguanidine To a solution of N-cyano-N'-phenylthiourea (1.7 g, 9.5 mmol) and the title B compound (1.6 g, 7.3 mmol) in dimethylformamide (7 mL), under argon was added 1-(3-dimethylaminopropyl)-2-ethylcarbodiimide hydrochloride (1.8 g, 9.5 mmol) at room temperature. The reaction mixture was stirred at room temperature for 2 hours and then partitioned between 1N hydrochloric acid and ethyl acetate. The organic phase was separated and the aqueous phase was reextracted with ethyl acetate. The combined extracts were washed with water, aqueous sodium bicarbonate and brine. After drying over anhydrous magnesium sulfate, the solvent was evaporated and the crude product was purified by flash chromatography on silica gel eluting with ethyl acetate/hexanes (7:3) to give a cololess solid (0.7 g). The solid was triturated with ether to yield the title compound (0.35 g), m.p. 214°–216° C.; $[\alpha_D]^{25} = -34.8°$ (c=0.417, MeOH): $^1$H NMR (DMSO-d$_6$) d 9.28 (s, 1 H), 7.58 (d, J=8.0 Hz, 3 H), 7.35 (m, 4 H), 7.15 (m, 1 H), 6.90 (d, J=8.2 Hz, 1 H), 5.92 (br s, 1 H), 4.92 (t, J=9.0 Hz, 1 H), 3.72 (br d, J=5.9 Hz, 1 H), 1.41, 1.18 (s, 3 H each); $^{13}$C NMR (DMSO-d$_6$) 159.2, 156.3, 137.5, 132.6, 132.5, 129.0, 124.8, 124.7, 123.6, 119.0, 117.8, 117.0, 102.6, 80.4, 70.9, 51.9, 26.6, 18.6; IR(KBr) 2226, 2179, 1609, 1582, 1491, 1267 cm$^{-1}$.

Analysis calc'd for C$_{20}$H$_{19}$N$_5$O$_2$.0.37 H$_2$O:
C, 65.26; H, 5.40; N, 19.02;
Found: C, 65.62; H, 5.36; N, 18.57.

EXAMPLE 19

(3R-trans)-N''-Cyano-N-(6-cyano-3,4-dihydro-3-hydroxy-2,2-dimethyl-2H-1-benzopyran-4-yl)-N'-phenylguanidine

A.

(3R-trans)-4-amino-3,4-dihydro-3-hydroxy-2,2-dimethyl-2H-1-benzopyran-6-carbonitrile To a solution of [3R-[3α,4β(S*)]]-N-(6-cyano-3,4-dihydro-3-hydroxy-2,2-dimethyl-2H-1-benzopyran-4-yl)-α-hydroxybenzeneacetamide, compound of Example 18, part A (2.8 g, 7.9 mmol) in dioxane (30 ml) were added concentrated sulfuric acid (2.5 g) and water (12 ml) at room temperature and the reaction mixture was heated at reflux temperature for 24 hours. It was concentrated in vacuo and the residue was combined with another batch of the same material and dissolved in ethyl acetate (400 ml). The resulting solution was washed with 1N sodium hydroxide (50 ml) followed by water (50 ml) and dried over anhydrous magnesium sulfate and concentrated in vacuo to give the title A compound (3.7 g) as an oil: $^1$H NMR (CDCl$_3$) δ 7.74 (s, 1 H), 7.42 (dd, J=2.0 & 6.0 Hz, 1 H), 6.82 (d, J=8.0 Hz, 1 H), 3.65 (d, J=10.0 Hz, 1 H), 3.36 (d, J=10.0 Hz, 1 H), 1.53 (s, 3 H), 1.23 (s, 3 H).

B.

(3R-trans)-N''-Cyano-N-(6-cyano-3,4-dihydro-3-hydroxy-2,2-dimethyl-2H-1-benzopyran-4-yl)-N'-phenylguanidine To a solution of N-cyano-N'-phenylthiourea (3.9 g, 21.9 mmol) and the title A compound (3.68 g, 16.9 mmol) in dimethylformamide (20 mL) under argon, 1-(3-dimethylaminopropyl)-2-ethylcarbodiimide hydrochloride (4.2 g, 21.9 mmol) was added at room temperature. The reaction mixture was stirred at room temperature for 2 hours and then partitioned between 1N hydrochloric acid and ethyl acetate. The organic phase was separated and the aqueous phase was reextracted with ethyl acetate. The combined extracts were washed with water, aqueous sodium bicarbonate and brine. After drying over anhydrous magnesium sulfate, the solvent was evaporated and the crude product was triturated with ethyl acetate-ether ether to give a colorless solid (3.5 g). The crude product was purified by flash chromatography on silica gel eluting with ethyl acetate/hexanes (7:3) and the solid, obtained after evaporation of the solvent, was triturated with ether to give the title compound (1.8 g) as a colorless solid, m.p. 215°–217° C., $[\alpha_D]^{25} = +34.8°$ (c=0.417, MeOH): $^1$H NMR (CDCl$_3$/DMSO-d$_6$) δ 8.8 (s, 1 H), 7.6 (s, 1 H), 7.44 (d, J=8.0 Hz, 1 H), 7.35 (d, J=5.0 Hz, 4 H), 7.22 (m, 1 H), 6.85 (d, J=8.8 Hz, 1 H), 6.7 (br s, 1 H), 5.0 (t, J=9.0 Hz, 1 H), 3.72 (br d, J=5.3 Hz, 1 H), 1.48, 1.18 (s, 3 H each); $^{13}$C NMR (CDCl$_3$/DMSO-d$_6$) 159.6, 156.5, 136.6, 132.5, 129.2, 125.7, 124.1, 123.7, 118.9, 118.1, 117.2, 103.4, 80.3, 72.8, 52.4, 26.4, 18.6; IR (KBr) 2226, 2179, 1609, 1582, 1491, 1267 cm$^{-1}$.

Analysis calc'd for C$_{20}$H$_{19}$N$_5$O$_2$.0.45 H$_2$O:
C, 65.01; H, 5.42; N, 18.95;
Found: C, 65.18; H, 5.47; N, 18.51.

EXAMPLE 20 is an alternate procedure to Example 18 and the procedure of this Example 20 is preferred. Additionally, the 3S, 4R enantiomer of Example 20 is the one of the preferred compounds of the present invention.

EXAMPLE 20

(3S-trans)-N''-Cyano-N-(6-cyano-3,4-dihydro-3-hydroxy-2,2-dimethyl-2H-1-benzopyran-4-yl)-N'phenylguanidine

A.

[3S-[3α,4β(S*)]]-N-(6-Cyano-3,4-dihydro-3-hydroxy-2,2-dimethyl-2H-1-benzopyran-4-yl)-α-hydroxybenzeneacetamide and

[3R-[3α,4β(R*)]]-N-(6-Cyano-3,4-dihydro-3-hydroxy-2,2-dimethyl-2H-1-benzopyran-4-yl)-α-hydroxybenzeneacetamide To a solution of (trans)-4-amino-3,4-dihydro-3-hydroxy-2,2-dimethyl-2H-1-benzopyran-6-carbonitrile (prepared according to Evans et al., J. Med. Chem., 1983, 26, 1582 and J. Med. Chem., 1986, 29, 2194) (1.64 g, 7.5 mmol),
R(-)-mandelic acid (1.14 g, 7.5 mmol),
hydroxybenzotriazole hydrate (1.0 g, 7.5 mmol) in dimethylformamide (15 ml) at 0° C. was added dicyclohexylcarbodiimide (1.55 g, 7.5 mmol) at room temperature. The reaction mixture was allowed to stir at room temperature for 20 hours and then cooled in an ice bath. The solid was removed by filtration and the filtrate was concentrated in vacuo. The residue was dissolved in 5% methanol in chloroform and washed with 1 N sodium hydroxide, 1 N hydrochloric acid, brine followed by drying over anhydrous magnesium sulfate. After removing drying agent the solvent was removed in vacuo. The residue was crystallized from ethanol to give

[3S-[3α,4β(S*)]]-N-(6-cyano-3,4-dihydro-3-hydroxy-2,2-dimethyl-2H-1-benzopyran-4-yl)-α-hydroxybenzeneacetamide (0.85 g) as a white solid, m.p. 235°–237° C.: $[\alpha_D]^{25} = -94.9°$ (c=1, MeOH); $^1$H NMR (DMSO-d$_6$) δ 8.45 (d, J=8.0 Hz, 1 H), 7.5 (m, 4 H), 7.3 (m, 2 H), 7.0 (s, 1 H), 6.88 (d, J=8.0 Hz, 1 H), 6.2 (s, 1 H), 5.57 (d, J=5.0 Hz, 1 H), 5.0 (s, 1 H), 4.76 (t, J=9.0 Hz, 1 H), 3.75 (dd, J=5.0 & 5.0 Hz, 1 H), 1.40 (s, 3 H), 1.15 (s, 3 H).

Analysis calc'd for C$_{20}$H$_{20}$N$_2$O$_4$:
C, 68.17; H, 5.72; N, 7.95;

Found: C, 68.00; H, 5.52; N, 7.95.

The residual material recovered from the mother liquor was purified by flash chromatography on silica gel eluting with hexane-ethyl acetate (3:7) and the product was crystallized from dichloromethane-isopropyl ether to give [3R-[3α,4β(R*)]]-N-(6-Cyano-3,4-dihydro-3-hydroxy-2,2-dimethyl-2H-1-benzopyran-4-yl)-α-hydroxybenzeneacetamide as a white solid, m.p. 100°-102° C. (foaming): $[\alpha_D]^{25} = +25.6°$ (c=1, MeOH): ;$^1$H NMR (CDCl$_3$) δ 7.4 (m, 5 H), 7.26 (t, J=1.0 Hz, 1 H), 6.97 (d, J=9.0 Hz, 1 H), 6.83 (d, J=9.0 Hz, 1 H), 5.16 (s, 1 H), 4.98 (t, J=9.0 Hz, 1 H), 3.8 (d, J=5.0 Hz, 1 H), 3.55 (dd, J=4.0 & 5.0 Hz, 1 H), 1.45 (s, 3 H), 1.2 (s, 3 H).

Analysis calc'd for $C_{20}H_{20}N_2O_4 \cdot 0.25\ H_2O$:
C, 67.30; H, 5.78; N, 7.84;
Found: C, 67.17; H, 5.87; N, 7.44.

B.
(3S-trans)-4-Amino-3,4-dihydro-3-hydroxy-2,2-dimethyl-2H-1-benzopyran-6-carbonitrile To a solution of [3S-[3α,4β(S*)]]-N-(6-cyano-3,4-dihydro-3-hydroxy-2,2-dimethyl-2H-1-benzopyran-4-yl)-o-hydroxybenzeneacetamide, title A compound (6.09 g, 17.0 mmol) in dioxane (60 ml) was added a solution of sulfuric acid (6.0 g) in water (30 ml) at room temperature and the reaction mixture was heated at reflux temperature for 24 hours. It was then concentrated in vacuo and the residue was dissolved in ethyl acetate. The organic layer was washed with 1N sodium hydroxide followed by water and dried over anhydrous magnesium sulfate. The solvent was evaporated to give the title B compound as an oil: $^1$H NMR (CDCl$_3$) δ 7.74 (s, 1 H), 7.42 (dd, J=2.0 & 6.0 Hz, 1 H), 6.82 (d, J=8.0 Hz, 1 H), 3.65 (d, J=10.0 Hz, 1 H), 3.36 (d, J=10.0 Hz, 1 H), 1.53 (s, 3 H), 1.23 (s, 3 H).

C.
(3S-trans)-N''-Cyano-N-(6-cyano-3,4-dihydro-3-hydroxy-2,2-dimethyl-2H-1-benzopyran-4-yl)-N'-phenylguanidine To a solution of N-cyano-N'-phenylthiourea (2.11 g, 11.9 mmol) and (3S-trans)-4-amino-3,4-dihydro-3-hydroxy-2,2-dimethyl-2H-1-benzopyran-6-carbonitrile (2.0 g, 9.1 mmol), title B compound, in dimethylformamide (20 mL) under argon was added 1-(3-dimethylaminopropyl)-2-ethylcarbodiimide hydrochloride (2.23 g, 11.9 mmol) at room temperature. The reaction mixture was stirred at room temperature for 2 hours and then partitioned between 1N hydrochloric acid and ethyl acetate. The organic phase was separated and the aqueous phase was reextracted with ethyl acetate. The combined organic extracts were washed with water, sodium bicarbonate and brine. After drying over anhydrous magnesium sulfate, the solvent was evaporated and the crude product was purified by flash chromatography on silica gel eluting with ethyl acetate/hexanes (7:3) to give a colorless solid which was triturated with ether to yield the title compound (0.35 g), m.p. 215°-216° C.: $[\alpha]_D^{25} = -33.5°$ (c=1, MeOH); $^1$H NMR (DMSO-d$_6$) δ 9.28 (s, 1 H), 7.58 (d, J=8.0 Hz, 3 H), 7.35 (m, 4 H), 7.15 (m, 1 H), 6.90 (d, J=8.2 Hz, 1 H), 5.92 (br s, 1 H), 4.92 (t, J=9.0 Hz, 1 H), 3.72 (br d, J=5.9 Hz, 1 H), 1.41, 1.18 (s, 3 H each); $^{13}$C NMR (DMSO-d$_6$) 159.2, 156.3, 137.5, 132.6, 132.5, 129.0 124.8, 124.7, 123.6, 119.0, 117.8, 117.0, 102.6, 80.4, 70.9, 51.9, 26.6, 18.6; IR (KBr) 2226, 2179, 1609, 1582, 1491, 1267 cm$^{-1}$.

Analysis calc'd for $C_{20}H_{19}N_5O_2 \cdot 0.24\ H_2O$:
C, 65.26; H, 5.40; N, 19.02;
Found: C, 65.62; H, 5.36; N, 18.57.
HPLC: 99.5% by Chiracel OD column/hexanes (80%), isopropanol (20%), formic acid (0.1%).

EXAMPLE 21

(trans)-4-[2-(Cyanoimino)tetrahydro-1(2H)-pyrimidinyl]-3,4-dihydro-3-hydroxy-2,2-dimethyl-2H-1-benzopyran-6-carbonitrile

A.
(trans)-4-[(3-Aminopropyl)amino]-3,4-dihydro-3-hydroxy-2,2-dimethyl-2H-1-benzopyran-6-carbonitrile To a suspension of 6-cyano-3,4-expoxy-3,4-dihydro-2,2-dimethyl-2H-benzopyran (prepared according to Evans et al., *J. Med. Chem.*, 1983, 26, 1582 and *J. Med. Chem.*, 1986, 29, 2194) (1.0 g, 5.0 mmol) in ethanol (5.0 mL), 1,3-diaminopropane (2.4 mL, 32.4 mmol) was added at room temperature and the reaction mixture was stirred at room temperature for 36 hours. The solvent was removed under reduced pressure and the residue was dried by use of a vacuum pump for 5 hours to yield the title A compound (1.3 g) as a colorless foam. This material was used for the next step without purification.

B.
(trans)-4-[2-(Cyanoimino)tetrahydro-1(2H)-pyrimidinyl]-3,4-dihydro-3-hydroxy-2,2-dimethyl-2H-1-benzopyran-6-carbonitrile To a solution of the title A compound (1.3 g, 4.7 mmol) in ethanol (5 ml) at room temperature, triethylamine (1.3 mL, 9.4 mmol) was added followed by dimethyl N-cyanodithioiminocarbonate (1.5 g, 9.4 mmol of 90%) with stirring at room temperature The reaction mixture was heated at 80° C. for 3 hours and then cooled to ambient temperature. The solvent was evaporated to give a light yellow foam (1.5 g). This material was taken up in methanol (20 mL) and the resulting suspension was treated with mercuric acetate (2.0 g, 6.1 mmol). The reaction mixture was stirred at room temperature for 2 hours and the solvent was evaporated under reduced pressure. The residue was diluted with water and alkalized to pH ~9.0 with 2.5N sodium hydroxide and the product was extracted with 10 percent methanolic chloroform (3×). The combined extract was washed with brine whereby a thick emulsion resulted. The two phase mixture was filtered through a celite pad and the organic layer was separated and dried over magnesium sulfate. The solvent was evaporated and the residue was purified by flash chromatography (5% methanol in chloroform) on silica gel to provide a colorless residue (0.5 g) which was crystallized from isopropyl ether-ethyl acetate to yield the title compound as a white powder, m.p. 152°-153° C.: $^1$H NMR (DMSO-d$_6$) δ 7.60 (d, J=7.0 Hz, 1 H), 7.40 (s, 1 H), 7.0 (d, J=9.0, 1 H), 5.85 (d, J=5.2 Hz, 1 H), 5.6 (d, J=10.5 Hz, 1 H), 3.8 (dd, J=5.0 Hz, 1 H), 3.2 (m, 4 H), 2.9 (br d, 1H), 1.54, 1.26 (s, 3 H each); $^{13}$C NMR (DMSO-d$_6$) 164.5, 156.8, 133.2, 131.6, 118.9, 118.2, 118.0, 103.1, 80.4, 67.3, 51.2, 40.3, 26.6, 18.6; IR (KBr) 1268.7, 1316.8, 1402.2, 1489.5, 1558.1, 1580.4, 2174.7, 3421.3 cm$^{-1}$.

Analysis calc'd for $C_{17}H_{19}N_5O_2 \cdot 0.42\ H_2O$:
C, 61.33; H, 6.01; N 21.04;
Found: C, 61.31; H, 6.02; N, 21.06.

EXAMPLE 22

(trans)-N''-Cyano-N-(6-cyano-3,4-dihydro-3-hydroxy-2,2-dimethyl-2H-1-benzopyran-4-yl)-N'-(4-pyridinylmethyl)guanidine A suspension of (trans)-4[[(cyanoimino)phenoxymethyl]amino-3,4-dihydroxy-2,2-dimethyl-2H-1-benzopyran-6-carbonitrile (1.0 g, 2.76 mmol), compound of Example 7, part A, in isopropanol (5 ml) was treated at room temperature with 4-(aminomethyl)pyridine (1.0 ml). The reaction mixture was allowed to stir at room temperature for 4 hours and then heated at reflux temperature for 16 hours. The reaction mixture was cooled to ambient temperature and the precipitated solid was filtered off. The product was recrystallized from ethyl acetate to give the title compound (0.76 g) as a colorless solid, m.p. 156°-158° C.: $^1$H NMR (DMSO-d$_6$) δ 8.53 (d, J=6.0 Hz, 2 H), 7.9 (m, 1 H), 7.5g (dd, J=3.0 & 6.0 Hz, 1 H), 7.44 (s, 2 H), 7.31 (d, J=6.0 Hz, 2 H), 6.91 (d, J=9.0 Hz, 1 H), 5.9 (s, 1 H), 4.87 (m, 1 H), 4.48 (t, J=2.0 & 6.0 Hz, 2 H), 3.7 (m, 1 H), 1.99 (s, 3 H), 1.18 (s, 3 H); $^{13}$C NMR (DMSO-d$_6$) 160.4, 156.2, 149.4, 132.6, 132.3, 124.7, 121.7, 117.8, 117.4, 102.6, 80.4, 71.0, 51.5, 43.4, 26.5, 18.6; IR (KBr) 1125.2, 1490.2, 1524.1, 1577.8, 1611.3, 2170.4, 2224.9, 3429.7 cm$^{-1}$.

Analysis calc'd for C$_{20}$H$_{20}$N$_6$O$_2$.0.2 H$_2$O:
C, 63.22; H, 5.41; N, 22.12;
Found: C, 63.42; H, 5.17; N, 21.92.

EXAMPLE 23

(trans)-N''-Cyano-N-(6-cyano-3,4-dihydro-3-hydroxy-2,2-dimethyl-2H-1-benzopyran-4-yl)-N'-(3-pyridinylmethyl)guanidine A suspension of (trans)-4-[[(cyanoimino)-phenoxymethyl]amino]-3,4-dihydroxy-2,2-dimethyl-2H-1-benzopyran-6-carbonitrile (1.0 g, 2.76 mmol), compound of Example 7, part A, in isopropanol (5 ml) was treated at room temperature with 3-(aminomethyl)pyridine (1.0 ml). The reaction mixture was allowed to stir at room temperature for 4 hours and then heated under reflux for 16 hours. The reaction mixture was concentrated in vacuo and the resulting solid was crystallized from ethyl acetate to give the title compound (0.72 g) as a colorless solid, m.p. 226°-228° C: $^1$H NMR (DMSO-d$_6$) δ 8.55 (s, 1 H), 8.49 (d, J=2.0 Hz, 2 H), 7.85 (m, 1 H), 7.75 (d, J=8.0 Hz, 1 H), 7.59 (d, J=8.0 Hz, 1 H), 7.40 (m, 3 H), 6.91 (d, J=8.0 Hz, 1 H), 5.85 (s, 1 H), 4.82 (m, 1 H), 4.48 (m, 2 H), 3.74 (m, 1 H), 1.40 (s, 3 H), 1.17 (s, 3 H); $^{13}$C NMR 160.43, 156.2, 148.6, 148.2, 134.6, 134.2, 132.7, 132.2, 124.8, 123.4, 118.9, 117.9, 117.5, 102.6, 80.4, 71.0, 51.5, 42.1, 26.6, 18.7; IR (KBr) 1125.2, 1490.1, 1524.1, 1577.8, 1611.3, 2170.4, 2224.9, 3429.7 cm$^{-1}$.

Analysis calc'd for C$_{20}$H$_{20}$N$_6$O$_2$0.17 H$_2$O:
C, 63.22; H, 5.41; N, 22.12;
Found C, 63.08; H, 5.32; N, 22.38.

EXAMPLE 24

(trans)-N''-Cyano-N-(6-ethynyl-3,4-dihydro-3-hydroxy-2,2-dimethyl-2H-1-benzopyran-4-yl)-N'-phenylguanidine

A. 1-((1,1-Dimethyl-2-propynyl)oxy)-4-iodobenzene

A solution of 3-chloro-3-methyl-1-butyne (10.0 g, 97.9 mmol), 4-iodophenol (15.0 g, 68.4 mmol), sodium hydroxide (3.90 g, 97.5 mmol) and tetrabutylammonium hydrogen sulfate (9.33 g, 27.5 mmol) in methylene chloride (50 mL) and water (50 mL) was stirred for 19 days at room temperature. After separating the two layers, the organic layer was washed with 1 N sodium hydroxide followed by water, dried over magnesium sulfate and concentrated in vacuo. The residue was dissolved in ethyl acetate and washed successively with 1 N hydrochloric acid, 1 N sodium hydroxide, water, brine and dried over anhydrous magnesium sulfate. After removing drying agent, the solvent was removed in vacuo. The crude product was purified by flash chromatography on silica gel eluting with toluene/hexane (1:10) to give the title compound as an oil (5.78 g, 20.2 mmol) in 30% yield: $^1$H NMR (CDCl$_3$) δ 7.56 (d, J=8.7 Hz, 2H), 6.98 (d, J=8.8 Hz, 2H), 2.56 (s, 1H), 1.63 (s, 6H); $^{13}$C NMR (CDCl$_3$) δ 155.4, 137.8, 123.5, 86.0, 85.6, 74.3, 72 6, 29.5.

B. 2,2-Dimethyl-6-iodo-2H-1-benzopyran

The title A compound (3.91 g, 13.7 mmol) was heated in an oil bath at 170° for 2 hours. After cooling, the crude product was purified by flash chromatography on silica gel eluting with toluene/hexane (1:20) to give the title compound as an oil (3.26 g, 11.4 mmol) in 83% yield: $^1$H NMR (CDCl$_3$) δ 7.34 (dd, J$_1$=1.8, J$_2$=2.4 Hz, 1H), 7.24 (d, J=0.9 Hz, 1H), 6.52 (d, J=8.8 Hz, 1H), 6.21 (d, J=10.0 Hz, 1H), 5.58 (d, J=10.0 Hz, 1H), 1.40 (s, 6H); $^{13}$C NMR (CDCl$_3$) δ 152.8, 137.5, 134.7, 131.6, 123.6, 121.1, 118.6, 82.4, 76.4, 27.9.

C. 2,2-Dimethyl-6-(trimethylsilyl)ethynyl)-2H-1-benzopyran

A solution of the title B compound (1.32 g, 4.61 mmol), trimethyl((trimethylstannyl)ethynyl)silane (1.60 g, 5.69 mmol), lithium chloride (0.62 g, 14.6 mmol) and tetrakis(triphenylphosphine) palladium (0.69 g, 0.60 mmol) in dioxane (16.5 mL) was stirred under argon for 5 hours in an oil bath at 65°. The reaction mixture was cooled to room temperature and concentrated in vacuo to give a residue that was combined with the material prepared in a similar manner on a 2.42 mmol scale. The combined material was rinsed with toluene/hexane (1:10) and the filtrate was concentrated in vacuo. The crude product was purified by flash chromatography on silica gel eluting with toluene/hexane (1:10) to give the title C cmpound as an oil (1.82 g, 7.00 mmol) in 4.1 Hz, 1H), 3.25 (d, J=4.1 Hz, 1H), 1.34 (s, 3H), 1.00 (s, 3H), 0.00 (s, 9H); $^{13}$C NMR (CDCl$_3$) δ 52.9, 134.1, 133.4, 120.0, 118.1, 103.6, 92.9, 3.6, 62.5, 50.5, 25.6, 22.7, 0.00.

E. (trans)-4-Amino-6-ethynyl-3,4-dihydro-2H-1-benzopyran-3-ol

A solution of the title D compound (0.53 g, 1.95 mmol) in ethanol (15 mL) and concentrated aqueous ammonium hydroxide (30 mL) was stirred at room temperature for 4 days. The solvent was removed in vacuo and the residue was purified by flash chromatography on silica gel eluting with hexane/ethyl acetate/-methanol (5:5:1) to give a partially purified product. This material was triturated with diethyl ether to give the title compound as a white solid (0.42 g, 1.93 mmol) in 99% yield, m.p. 132°-134° C.: $^1$H NMR (CDCl$_3$) δ 7.62 (s, 1H), 7.38 (dd, J$_1$=1.2, J$_2$=1.8 Hz, 1H), 6.82 (d, J=8.2, Hz, 1H), 3.73 (d, J=10.0 Hz, 1H), 3.45 (d, J=9.4 Hz, 1 H), 3.10 (s, 1H), 2.56 (br s, 3H), 1.59 (s, 3H), 1.30 (s, 3H); $^{13}$C NMR (CDCl$_3$) δ 153.0, 132.6, 131.0, 125.7, 117.2, 14.0, 83.6 78.6, 75.9, 75.8, 51.1, 26.9, 18.7.

Analysis calc'd for C$_{13}$H$_{15}$NO$_2$.0.06 H$_2$O:

C, 71.52; H, 6.98; N, 6.42;
Found: C, 71.47; H, 6.95; N, 6.47.

F.
(trans)-N''-Cyano-N-(6-ethynyl-3,4-dihydro-3-hydroxy-2,2-dimethyl-2H-1-benzopyran-4-yl)-N'-phenylguanidine To a solution of the title E compound (0.150 g, 0.69 mmol) and N-cyano-N'-phenylthiourea 100% yield: $^1$H NMR (CDCl$_3$) δ 6.98 (dd, J$_1$ =2.3, J$_2$=8.2 Hz, 1H), 6.87 (d, J=1.8 Hz, 1H), 6.44 (d, J=8.2 Hz, 1H), 6.02 (d, J=9.4 Hz, 1H), 5.38 (d, J=10.0 Hz, 1H), 1.20 (s, 6H), 0.00 (s, 9H); $^{13}$C NMR (CDCl$_3$) δ 153.4, 133.0, 131.2, 130.0, 121.6, 121.0, 116.3, 115.2, 105.2, 92.1, 76.7, 28.1, 0.1.

Analysis calc'd for C$_{16}$H$_{20}$OSi:
C, 74.94; H, 7.86;
Found: C, 75.19; H, 7.61.

D.
(cis)-1a,7b-Dihydro-2,2-dimethyl-6-((tri-methylsilyl)ethynyl)-2H-oxireno(c)-(1)-benzopyran To a solution of the title C compound (1.37 g, 5.34 mmol) and sodium bicarbonate (2.33 g, 27.7 mmol) in methylene chloride (27 mL) and water (27 mL) at 0° was added 3-chloroperoxybenzoic acid (1.51 g of 80–85% purity, 7.01 mmol). After a few minutes of stirring, the ice bath was removed and the reaction mixture was stirred at room temperature for 9 hours. After adding methylene chloride to the reaction mixture, the organic layer was separated and washed with water followed by brine, dried over magnesium sulfate and concentrated in vacuo. The crude product was purified by flash chromatography on silica gel eluting with hexane/ethyl acetate (10:1) to give recovered starting material (0.47 g) and the title compound as an oil (0.53 g, 1.95 mmol) in 36% yield: $^1$H NMR (CDCl$_3$) δ0 7.24 (d, J=1.8 Hz, 1H), 7.11 (dd, J$_1$=1.78, J$_2$=2.3 Hz, 1H), 6.49 (d, J=8.2 Hz, 1H), 3.62 (d, J= (0.180 g, 1.0 mmol) in dimethylformamide (5 mL) was added 1-(3-dimethylaminopropyl)-2-ethylcarbodiimide hydrochloride (0.200 g, 1.0 mmol) at room temperature. The reaction mixture was stirred overnight at room temperature and the solvent was removed in vacuo. The residue was partitioned between water and ethyl acetate. The organic layer was separated and dried over sodium sulfate. The solvent was removed in vacuo and the residue was purified by flash chromatography on silica gel eluting with hexane/ethyl acetate/ethanol (30:10:5) to give a partially pure product. This material was triturated with diethyl ether to give the title compound (0.12 g, 0.34 mmol) in 49% yield, m.p. 220°–222° C. (dec); $^1$H NMR (CDCl$_3$) δ 7.20–7.40 (m, 7H), 6.70 (d, J=8.2 Hz, 1H), 5.00 (d, J=10.0 Hz, 1H), 3.67 (d, J=9.4 Hz, 1H), 3.34 (s, 1H), 1.44 (s, 3H), 1.24 (s, 3H); $^{13}$C NMR (CDCl$_3$) δ 161.6, 154.6, 138.2, 133.7, 132.8 130.5, 127.2, 125.7, 123.9, 118.9, 118.3, 116.0, 84.3, 80.5, 77.2, 74.6, 54.0, 27.1, 18.6.

Analysis calc'd for C$_{21}$H$_{20}$N$_4$O$_2$.0.32 H$_2$O:
C, 68.89; H, 5.68; N, 15.31;
Found: C, 69.11; H, 5.55; N, 15.09.

EXAMPLE 25
(trans)-N''-Cyano-N-(3,4-dihydro-6-(phenylethynyl)-2H-1-benzopyran-4-yl)-N'-phenylguanidine A. 2,2-Dimethyl-6-(phenylethynyl)-2H-1-benzopyran To a solution of the title B compound from Example 24 (1.69 g, 5.91 mmol) and phenylacetylene (2.0 mL, 18.1 mmol) in diethylamine (30 mL) at room temperature were added bis(triphenylphosphine)palladium(II)-chloride (0.40 g, 0.572 mmol) and copper(I) iodide (0.22 g, 1.41 mmol) under argon atmosphere. After stirring for 1 hour at room temperature, the reaction mixture was concentrated under reduced pressure. The residue was dissolved in ethyl acetate and the insoluble material was filtered. The filtrate was concentrated in vacuo. The residue was again dissolved in toluene/hexane (1:10) and the insoluble material was filtered. The filtrate was concentrated in vacuo and the crude product was purified by flash chromatography on silica gel eluting with toluene/hexane (1:10) to give the title compound as an oil (1.43 g, 5.49 mmol) in 92% yield: $^1$H NMR (CDCl$_3$) δ 7.47–7.50 (m, 2H), 7.24–7.31 (m, 4H), 7.14 (d, J=2.4 Hz, 1H), 6.72 (d, J=8.2 Hz, 1H), 6.26 (d, J=10.0 Hz, 1H), 5.58 (d, J=9.4 Hz, 1H), 1.40 (s, 6H); $^{13}$C NMR (CDCl$_3$) δ 153.2, 132.5, 131.3, 131.2, 129.5, 128.2, 127.8, 123.6, 121.6, 121.1, 116.4, 115.2, 89.4, 87.8, 76.7, 28.0.

B.
2,2-Dimethyl-6-(phenylethynyl)-2H-oxireno-(c)-(1)-benzopyran

To a solution of the title A compound (1.14, 4.38 mmol) and sodium bicarbonate (1.86 g, 22.1 mmol) in methylene chloride (15 mL) and water (15 mL) at 0° was added 3-chloroperoxybenzoic acid (1.21 g of 80–85% purity, 5.62 mmol). After 5 minutes, the ice bath was removed and the reaction mixture was stirred at room temperature for 8 hours. It was diluted with methylene chloride and the organic layer was taken. It was washed with water followed by brine and dried over magnesium sulfate. The solvent was concentrated in vacuo and the material was purified by flash chromatography on silica gel eluting with hexane/ethyl acetate (10:1) to give recovered starting material (0.17 g) and the title compound as an oil (0.74 g, 2.68 mmol) in 61% yield: $^1$H NMR (CDCl$_3$) δ 7.42–7.64 (m, 7H), 6.90 (d, J=8.8 Hz, 1H), 3.99 (d, J=4.7 Hz, 1H), 3.60 (d, J=4.7 Hz, 1H), 1.69 (s, 3H), 1.3B (s, 3H) $^{13}$C NMR (CDCl$_3$) δ 152.8. 133.7, 132.9, 131.4, 128.3, 128.0, 123.4, 120.2. 118.2. 115.9, 88.9. 88.3, 73.6 62.5, 50.6. 48.2, 22.7.

C.
(trans)-4-Amino-3,4-dihydro-2,2-dimethyl-6-(phenylethynyl)-2H-1-benzopyran-3-ol A solution of the title B compound (0.71 g, 2.55 mmol) in absolute ethanol (20 mL) and concentrated aqueous ammonium hydroxide (40 mL) was stirred for 7 days and the solvents were removed in vacuo. The crude product was triturated with hexane and diisopropyl ether to give the title compound as a white solid (0.64 g, 2.18 mmol) in 86% yield, m.p. 162°–164° C.; $^1$H NMR (CDCl$_3$) δ 7.36–7.67 (m, 7H), 6.86 (d, J=8.2 Hz, 1H), 3.7B (d, J=10.0 Hz, 1H), 3.48 (d. J=10.0 Hz, 1H), 2.51 (br s, 3H), 1.62 (s, 3H), 1.32 (s, 3H); $^{13}$C NMR (CDCl$_3$) δ 152.7, 132.1, 131.4, 130.4, 128.3, 128.0. 125.6, 122.8, 117.3, 115.0, 88.6, 87.1, 78.5. 76.0, 51.2, 26.9, 18.7..

Analysis calc'd for C$_{19}$H$_{19}$O$_2$N.0.28 H$_2$O:
C, 76.46; H, 6.61; N, 4.69;
Found: C, 76.39; H, 6.52; N, 4.76.

D.
(trans)-N″-Cyano-N-(3,4-dihydro-6-(phenylethynyl)-2H-1-benzopyran-4-yl)-N′-phenylguanidine To a solution of the title C compound (0.64 g, 2.18 mmol) and N-cyano-N′-phenylthiourea (0.56 g, 3.16 mmol) in dimethylformamide (16 mL) was added 1-(3-dimethylaminopropyl)-2-ethyl-carbodiimide hydrochloride (0.60 g, 3.49 mmol) at room temperature. The reaction mixture was stirred at room temperature for 2 days and the solvent was removed in vacuo. The residue was partitioned between ethyl acetate and water. The organic layer was taken and it was washed with water followed by brine, dried over sodium sulfate and concentrated in vacuo. The residue was purified by flash chromatography on silica gel eluting with hexane/ethyl acetate/ethanol (10:10:1) to give a partially purified material. This material was triturated with diisopropyl ether to give the title compound as a white solid (0.46 g, 1.05 mmol) in 48% yield, m.p. 175°–177° C.: $^1$H NMR (DMSO-$d_6$) δ 9.42 (s, 1H), 7.82 (d, J=8.8 Hz, 1H), 7.20–7.75 (m, 14H), 6.88 (d, J=9.4 Hz, 1H), 5.59 (br s, 1H), 5.02 (dd, $J_1$=8.8, $J_2$=9.4 Hz, 1H), 3.80 (br d, J=9.4 Hz, 1H), 1.50 (s, 3H), 1.27 (s, 3H); $^{13}$C NMR (DMSO-$d_6$) δ 159.5, 153.2, 138.0, 132.2, 131.6, 131.3, 129.3, 129.0, 128.0, 124.9, 124.1, 123.7, 122.9, 117.4, 114.3, 89.7, 88.3, 79.9, 71.6, 52.5, 27.1, 18.8.

EXAMPLE 26
(trans)-N″-Cyano-N-(3-4-dihydro-3-hydroxy-2,2-dimethyl-6-nitro-2H-1-benzopyran-4-yl)-N′-phenylguanidine To a solution of trans-4-amino-3,4-dihydro-3-hydroxy-2,2-dimethyl-6-nitro-2H-1-benzopyran (2.0 g, 8.39 mmoles, prepared according to Evans et al., *J. Med. Chem.*, 1983, 26, 1582 and *J. Med. Chem.*, 1986, 29, 2194) and N-cyano-N′-phenyl thiourea (1.93 g, 10.91 mmoles) in N,N-dimethylformamide (10 ml) was added 1-(3-dimethylamino-propyl)-2-ethylcarbodiimide HCl (2.09 g, 10.91 mmoles). The reaction mixture was stirred for 2 hours under argon at room temperature and partitioned between ethyl acetate and 5% hydrogen chloride solution. The aqueous phase was extracted with ethyl acetate; the combined organic layers were washed successively with distilled water, saturated sodium hydrogen carbonate solution, saturated sodium chloride solution and dried over anhydrous magnesium sulfate. The solvent was recovered under vacuum to obtain 2.79 g of crude product. This was twice recrystallized from the minimum amount of hot ethanol to obtain 1.01 g of the title compound as an off-white solid. The combined mother liquors were chromatographed on silica eluting with 1:1 ethyl acetate/hexane to afford an additional 0.49 g of product. $^1$H NMR (DMSO-$d_6$) δ 9.39 (broad s, 1H), 8.07 (s, 1H), 8.03 (d, J=2.35 Hz, 1H), 7.69 (d, J=8.21 Hz, 1H), 7.40–7.34 (m, 4H), 7.18–7.14 (m, 1H), 6.96 (d, J=8.80 Hz, 1H), 5.96 (broad s, 1H), 4.98 (m, 1H), 3.77 (d, J=9.39 Hz, 1H), 1.45 (s, 3H), 1.22 (s, 3H). $^{13}$C NMR (DMSO-$d_6$) δ 159.18, 158.14, 140.63, 137.44, 129.06, 124.77, 124.48, 124.33, 123.99, 123.47, 117.54, 116.90, 81.00, 70.60, 51.97, 26.51, 18.62.

Analysis calc'd for $C_{19}H_{19}N_5O_4$:
C, 59.83; H, 5.02; N, 18.37;
Found: C, 59.60; H, 4.93; N, 18.29.

EXAMPLE 27
(trans)-N″-Cyano-N-(6-cyano-3,4-dihydro-3-hydroxy-2,2-dimethyl-2H-1-benzopyran-4-yl)-N′-(4-cyanophenyl)guanidine

A. N-Cyano-N′-4-cyanophenylthiourea

The suspension of monosodium cyanamide (4.3 g, 67.2 mmol) in absolute ethanol (170 mL) was slowly treated with 4-cyanophenylisothiocyanate (10.75 g, 67.2 mmol). The reaction was allowed to stir at room temperature for 1 hour and then heated at 75° C. for 4 hours. The reaction was cooled to room temperature and the colorless solid was filtered and washed with ethanol to give the title A compound (10.0 g), m.p. >250° C.

B. (trans)-N″-Cyano-N-(6-cyano-3,4-dihydro-3-hydroxy-2,2-dimethyl-2H-1-benzopyran-4-yl)-N′-(4-cyanophenyl)guanidine The solution of the title A compound (1.2 g, 5.96 mmol) and (trans)-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.* 1986, 29, 2194) in dimethylformamide (5 mL) under argon was treated with 1-(3-dimethylaminopropyl)-2-ethylcarbodiimide hydrochloride (1.17 g, 5.96 mmol). The reaction was stirred at room temperature for 2 hours and then partitioned between 1N hydrogen chloride and ethyl acetate. The aqueous phase was reextracted with ethyl acetate and the combined extracts were washed with water, sodium bicarbonate and brine. After drying over anhydrous magnesium sulfate, the solvent was evaporated and the colorless residue was crystallized from ethyl acetate to yield the title compound (0.52 g), m.p. 261°–262° C. $^1$H NMR (DMSO-$d_6$) δ 8.24 (m, 3H), 7.63 (m, 3H), 6.94 (d, J=8.7 Hz, 1H), 6.1 (br s, 1H), 4.92 (t, J=9.0 Hz, 1H), 3.68 (br d, J=5.2 Hz, 1H), 1.44, 1.20 (s, 3H each). $^{13}$C NMR (DMSO-$d_6$) δ 158.7, 156.3, 145.1, 142.4, 132.9, 124.9, 124.0, 121.2, 119.1, 117.9, 116.3, 102.7, 80.4, 70.9, 51.9, 26.6, 18.6. IR (KBr) 3421.9, 2226.0, 2183.6, 1612.6, 1587.5, 1491.1, 1265.4 cm$^{-1}$.

Analysis calc'd for $C_{21}H_{18}N_6O_2 \cdot 0.44\ H_2O$:
C, 63.96; H, 4.82; N, 21.32;
Found: C, 64.36; H, 4.65; N, 20.94.

EXAMPLE 28
(trans)-N″-Cyano-N-(6-cyano-3,4-dihydro-3-hydroxy-2,2-dimethyl-2H-1-benzopyran-4-yl)-N′-(4-methoxyphenyl)guanidine

A. N-Cyano-N′-(4-methoxy)phenylthiourea

The suspension of monosodium cyanamide (1.95 g, 30.3 mmol) in absolute ethanol (50 mL) was slowly treated with 4-methoxyphenylisothiocyanate (5.0 g, 30.3 mmol). The reaction was allowed to stir at room temperature for 1 hour and then heated at 75° C. for 4 hours. The reaction was cooled to room temperature and the colorless solid was filtered and washed with ethanol to give the title A compound (5.4 g), m.p. >250° C.

B.
(trans)-N''-Cyano-N-(6-cyano-3,4-dihydro-3-hydroxy-2,2-dimethyl-2H-1-benzopyran-4-yl)-N'-(4-methoxyphenyl)guanidine The solution of the title A compound (1.23 g, 5.96 mmol) and (trans)-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.* 1986, 29, 2194) in dimethylformamide (5 mL) under argon was treated with 1-(3-dimethylamino-propyl)-2-ethylcarbodiimide hydrochloride (1.17 g, 5.96 mmol). The reaction was stirred at room temperature for 2 hours and then partitioned between 1N hydrogen chloride and ethyl acetate. The aqueous phase was reextracted with ethyl acetate and the combined extracts were washed with water, sodium bicarbonate and brine. After drying over anhydrous magnesium sulfate, the solvent was evaporated and the colorless residue was crystallized from ethyl acetate to yield the title compound (0.53 g), m.p. 228°–229° C. $^1$H NMR (DMSO-$d_6$) δ 9.15 (s, 1H), 7.66 (m, 2H), 7.33 (d, J=9.4 Hz, 3H), 6.99 (t, J=8.8 & 8.2 Hz, 3H), 5.88 (br s, 1H), 4.97 (t, J=8.8 & 9.4 Hz, 1H), 3.83 (s, 3H), 3.38 (m, H), 1.48, 1.25 (s, 3H each). $^{13}$C NMR (DMSO-$d_6$) δ 159.6. 157.1, 156.2, 132.5, 132.3, 131.6, 129.6, 126.6, 125.0, 117.8, 114.2, 102.5, 80.4, 70.6, 55.2, 51.6, 26.6, 18.5. IR (KBr) 2978.3, 2179.7, 1579.8, 1491.1, 1244.2 cm$^{-1}$.

Analysis calc'd for $C_{21}H_{21}N_5O_3$:
C, 64.43; H, 5.41; N, 17.90;
Found: C, 64.12; H, 5.36; N, 17.82.

EXAMPLE 29
N''-Cyano-N-(6-cyano-3,4-dihydro-2,2-dimethyl-2H-1-benzopyran-4-yl)-N'-phenylguanidine

A. 6-Cyano-3,4-dihydro-2,2-dimethyl-2H-1-benzopyran

A solution of 6-cyano-2,2-dimethyl-2H-1-benzopyran (5.5 g, 29.7 mmoles, prepared according to Evans et al., *J. Med. Chem., 1983, 26, 1582* and *J. Med. Chem.* 1986, 29, 2194) in anhydrous ethanol (40 ml) was treated with palladium on carbon (0.35 g) and stirred under hydrogen gas for 2 hours. The catalyst was filtered through celite and the filter cake washed with ethyl acetate. The filtrate was concentrated under vacuum to obtain 5.71 g of a yellow oil. The crude product was dissolved in ethyl acetate (60 ml) and washed successively with 5% hydrogen chloride solution (60 ml), saturated sodium hydrogen carbonate solution (60 ml), saturated sodium chloride solution (60 ml) and dried over anhydrous magnesium sulfate. The solvent was recovered under vacuum to yield 5.14 g of the title A compound as a yellow solid (m.p. 30°–31° C.) which was used in the next step without further purification. $^1$H NMR (CDCl$_3$) δ 7.37 (s, 1H), 7.34 (s, 1H), 6.80 (d, J=8.8 Hz, 1H), 2.78 (dd, 2H), 1.80 (dd, 2H), 1.35 (s, 6H). $^{13}$C NMR (CDCl$_3$) δ 157.95, 133.82, 131.34, 122.07, 119.53, 118.24, 102.66, 75.76, 32.13. 26.81. 22.06.

Analysis calc'd for $C_{12}H_{13}NO$:
C, 76.98; H, 7.00; N, 7.48;
Found: C, 77.03; H, 7.02; N, 7.58.

B. 4-Bromo-6-cyano-3,4-dihydro-2,2-dimethyl-2H-1-benzopyran

To a solution of the title A compound (6.40 g, 34.18 mmoles) in carbon tetrachloride (90 ml) was added N-bromosuccinimide (6.69 g, 37.6 mmoles, 1.1 eq.). The solution was purged with argon. A solution of azobisisobutyronitrile (0.4 g, 3.42 mmoles) in carbon tetrachloride (10 ml) was added; the reaction was heated at reflux for ¼ hour with irradiation (high intensity visible light). The reaction mixture was concentrated under vacuum and the residue was dissolved in 75 ml ethyl acetate. The solution was washed successively with distilled water (4×75 ml), saturated sodium hydrogen carbonate solution (75 ml), saturated sodium chloride solution (75 ml), and dried over anhydrous magnesium sulfate. The solvent was recovered under vacuum to obtain 9.51 g of an orange waxy solid which was triturated with cold pentane to provide 7.19 g of a beige solid. This was crystallized from ca. 25 ml of ethyl acetate in hexane (10:90) to yield 4.60 g of the title B compound as off-white needles, m.p. 94°–95° C. The mother liquors were combined and chromatographed on silica gel eluting with hexane/ethyl acetate (19:1) to afford an additional 2.26 g of product. $^1$H NMR (CDCl$_3$) δ 7.86 (d, J=1.17 Hz, 1H), 7.42 (dd, J=1.76 and 8.79 Hz, 1H), 6.82 (d, J=8.80 Hz, 1H), 5.35 (dd, 1H), 2.45 (m, 2H), 1.51 (s, 3H), 1.31 (s, 3H). $^{13}$C NMR (CDCl$_3$) δ 156.71, 136.25, 133.21, 122.61, 118.87, 103.81, 76.54, 43.57, 40.34, 28.36, 25.45.

Analysis calc'd for $C_{12}H_{12}NBrO$:
C, 54.16; H, 4.54; N, 5.26; Br, 30.02;
Found: C, 54.55; H, 4.62; N, 5.46; Br, 29.86.

C. 4-Azido-6-cyano-3,4-dihydro-2,2-dimethyl-2H-1-benzopyran

A solution of the title B compound (6.73 g, 25.29 mmoles) in dry N,N-dimethylformamide (100 ml) was treated with sodium azide (3.79 g, 50.57 mmoles, 2 eq.) and stirred at room temperature under argon for 4 hours. The reaction mixture was partitioned between 100 ml ethyl acetate and 200 ml distilled water. The organic layer was separated and the aqueous layer was extracted with 100 ml of ethyl acetate. The combined organics were washed successively with distilled water, saturated sodium hydrogen carbonate solution, saturated sodium chloride solution and dried over anhydrous magnesium sulfate. The solvent was evaporated under vacuum to obtain 5.62 g of orange gum which was triturated with pentane to provide 4.50 g of the title C compound as an off-white solid, m.p. 63°–64° C. $^1$H NMR (CDCl$_3$) δ 7.69 (s, 1H), 7.46 (d, J=8.80 Hz, 1H), 6.86 (d, J=8.21 Hz, 1H), 4.59 (dd, J=6.45 and 2.34 Hz, 1H), 2.24 (m, 1H), 2.01 (m, 1H), 1.49 (s, 3H), 1.36 (s, 3H). $^{13}$C NMR (CDCl$_3$) δ 157.66, 133.79, 133.41, 121.20, 119.24, 104.21, 76.80, 53.73, 38.30, 28.97, 26.29.

D. 4-Amino-6-cyano-3,4-dihydro-2,2-dimethyl-2H-1-benzopyran

A solution of the title C compound (2.00 g, 8.77 mmole) in absolute ethanol (50 ml) was treated with 10% palladium on carbon (0.25 g) and stirred under hydrogen gas for 1.25 hours at room temperature. The reaction mixture was filtered to remove the catalyst. The filtrate was acidified to pH 1–2 with concentrated hydrogen chloride (0.85 ml) and concentrated under vacuum to a white solid. The crude amine hydrogen chloride was dissolved in 100 ml distilled water and extracted with ethyl acetate (discarded). The aqueous layer was adjusted to pH 11–12 with 50% sodium hydroxide solution and extracted with ethyl acetate. The extracts were washed with saturated sodium chloride solution and dried over sodium sulfate. The solvent was evaporated under vacuum to provide 1.542 g of the title D compound as a yellow oil which solidified upon standing. The product was used in the next step without further purification. $^1$H NMR (DMSO-$d_6$) δ 8.01 (s, 1H), 7.51 (d, J=8.21 Hz, 1H), 6.82 (d, J=8.21 Hz, 1H), 3.86 (dd, 1H), 2.07 (dd, J=5.87 and 13.49 Hz, 1H), 1.56 (m, 1H), 1.39 (s, 3H), 1.24 (s, 3H). $^{13}$C NMR (DMSO-$d_6$) δ 156.82, 132.51, 131.59, 129.40, 119.47, 117.45, 101.70, 76.99, 43.13, 42.47, 29.39, 24.70.

E.
N'''-Cyano-N-(6-cyano-3,4-dihydro-2,2-dimethyl-2H-1-benzopyran-4-yl)-N'-phenylguanidine A solution of the title D compound (1.3 g, 6.43 mmoles), N-cyano-N'-phenylthiourea (1.48 g, 8.36 mmoles) and 1-(3-dimethylaminopropyl)-2-ethylcarbodiimide.HCl (1.60 g, 8.36 mmoles) in N,N-dimethylformamide (6.5 ml) was stirred at room temperature under argon for two hours. The reaction mixture was partitioned between ethyl acetate and a 5% hydrogen chloride solution. The aqueous layer was extracted with ethyl acetate. The combined organics were washed with distilled water, saturated sodium hydrogen carbonate solution, saturated sodium chloride solution, dried over sodium sulfate, and concentrated in vacuo to recover 1.67 g of an off-white solid. The crude material was chromatographed on silica gel eluting with hexane/ethyl acetate (1:1). Like fractions were combined and evaporated to yield 1.24 g of an off-white solid. This was recrystallized from the minimum amount of hot ethanol to obtain 780 mg of the title compound as a white solid, m.p. 223°–225° C. $^1$H NMR (DMSO-$d_6$) δ 9.31 (s, 1H), 7.68 (s, 1H), 7.56 (m, 2H), 7.34 (m, 4H), 7.18 (m, 1H), 6.89 (d, J=8.79 Hz, 1H), 5.18 (m, 1H), 2.19 (m, 1H), 1.90 (m, 1H), 1.40 (s, 3H), 1.30 (s, 3H). $^{13}$C NMR (DMSO-$d_6$) δ 158.26, 157.22, 137.38, 132.51, 132.17, 128.94, 124.94, 124.05, 123.82, 119.09, 118.09, 116.76, 102.10, 77.17, 44.48, 37.57, 29.13, 24.15.

Analysis calc'd for $C_{20}H_{19}N_5O.0.2\ H_2O$:
C, 68.83; H. 5.60; N, 20.07;
Found: C, 68.96; H, 5.43; N, 19.82.

EXAMPLE 30
(trans)-N'''-Cyano-N-(6-cyano-3,4-dihydro-3-hydroxy-2,2-dimethyl-2H-1-benzopyran-4-yl)-N'-(4-nitrophenyl)guanidine

A. N-Cyano-N'-4-nitrophenylthiourea

The suspension of monosodium cyanamide (6.4 g, 100 mmol) in absolute ethanol (170 mL) was slowly treated with (4-nitrophenyl)isothiocyanate (12.5 mL, 104.5 mmol). The reaction was allowed to stir at room temperature for 1 hour and then heated at 75° C. for 4 hours. The reaction was cooled to room temperature and the colorless solid was filtered and washed with ethanol to give the title A compound (13.6 g), m.p. >250° C.

B.
(trans)-N'''-Cyano-N-(6-cyano-3,4-dihydro-3-hydroxy-2,2-dimethyl-2H-1-benzopyran-4-yl)-N'-(4-nitrophenyl)guanidine The solution of the title A compound (1.3 g, 5.96 mmol) and (trans)-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.* 1986, 29, 2194) in dimethylformamide (5 mL) under argon was treated with 1-(3-dimethylaminopropyl)-2-ethylcarbodiimide hydrochloride (1.17 g, 5.96 mmol). The reaction was stirred at room temperature for 2 hours and then partitioned between 1N hydrogen chloride and ethyl acetate. The aqueous phase was reextracted with ethyl acetate and the combined extracts were washed with water, sodium bicarbonate and brine. After drying over anhydrous magnesium sulfate, the solvent was evaporated and the residue was flash chromatographed on silica gel with a mixture of hexane/ethyl acetate (3:7) followed by chloroform/methanol (8:2) to give 0.6 g of product. The resulting product was triturated with ethyl acetate to yield the title compound as a colorless solid, m.p. 250°–251° C. (foaming). $^1$H NMR (DMSO-$d_6$) δ 8.23 (d, J=8.8 Hz, 1H), 7.88 (d, J=8.8 Hz, 2H), 7.71 (d, J=8.8 Hz, 2H), 7.58 (d, J=7.6 Hz,=2H), 7.01 (d, J=8.8 Hz, 1H), 6.10 (br s, 1H), 5.01 (t, J=8.7 & 9.4 Hz, 1H), 3.79 (m, 1H), 1.51, 1.28 (s, 3H each). $^{13}$C NMR (DMSO-$d_6$) δ 158.8, 156.3, 142.9, 133.3, 132.9, 124.2, 122.1, 119.1, 117.9, 105.5, 102.7, 80.4, 70.9, 51.9, 26.6, 18.6. IR (KBr) 3387.2, 2986.0, 2224.1, 2185.5, 1612.6, 1568.2, 1520.0, 1342.5, 1265.4 cm$^{-1}$.

Analysis calc'd for $C_{20}H_{18}N_6O_4.0.75H_2O$:
C, 57.2I; H, 4.68; N, 20.02;
Found: C, 57.35; H, 4.36; N, 19.71.

EXAMPLE 31
(trans)-N-(4-Chlorophenyl)-N''-cyano-N-(6-cyano-3,4-dihydro-3-hydroxy-2,2-dimethyl-2H-1-benzopyran-4-yl)guanidine

A. N-Cyano-N'-(4-chlorophenyl)thiourea

The suspension of monosodium cyanamide (1.9 g, 29.4 mmol) in absolute ethanol (50 mL) was slowly treated with 4-chlorophenylisothiocyanate (5.0 g, 29.4 mmol). The reaction was allowed to stir at room temperature for 1 hour and then heated at 75° C. for 4 hours. The reaction was cooled to room temperature and the colorless solid was filtered and washed with ethanol to give the title A compound (5.4 g), m.p. >250° C.

B.
(trans)-N-(4-Chlorophenyl)-N''-cyano-N-(6-cyano-3,4-dihydro-3-hydroxy-2,2-dimethyl-2H-1-benzopyran-4-yl)guanidine The solution of the title A compound (1.26 g, 5.96 mmol) and (trans)-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.* 1986, 29, 2194) in dimethylformamide (5 mL) under argon was treated with 1-(3-dimethylamino-propyl)-2-ethylcarbodiimide hydrochloride (1.17 g, 5.96 mmol). The reaction was stirred at room temperature for 2 hours and then partitioned between 1N hydrogen chloride and ethyl acetate. The aqueous phase was reextracted with ethyl acetate and the combined extracts were washed with water, sodium bicarbonate and brine. After drying over anhydrous magnesium sulfate, the solvent was evaporated and the residue was purified by flash chromatography eluting with mixture of ethyl acetate/hexane (7:3). The solid was triturated with ethyl acetate to yield 0.7 g of the title compound, m.p. 216°–218° C. $^1$H NMR (DMSO-$d_6$) δ 9.43 (s, 1H), 7.68 (m, 3H), 7.45 (m, 4H), 6.95 (d, J=8.8 Hz, 1H), 5.99 (br s, 1H), 4.98 (t, J=9.4 &

8.8 Hz, 1H), 3.79 (m, 1H), 1.50, 1.27 (s, 3H each). $^{13}$C NMR (DMSO-d$_6$) δ 159.1, 156.2, 136.5, 132.6, 132.5, 128.8, 125.5, 124.6, 119.0, 117.8, 116.8, 102.6, 80.4, 70.9, 51.9, 26.5, 18.5. IR (KBr) 3400.7, 2226.0, 2181.6, 1606.8, 1575.9, 1491.1, 1267.3 cm$^{-1}$.

Analysis calc'd for C$_{20}$H$_{18}$ClN$_5$O$_2$:
C, 60.68; H, 4 58; N, 17.70; Cl, 8.96;
Found: C, 60.40; H, 4.70; N, 17.55; Cl, 8.68.

EXAMPLE 32

(trans)-N''-Cyano-N-(6-cyano-3,4-dihydro-3-hydroxy-2,2-dimethyl-2H-1-benzopyran-4-yl)-N'-(2-pyridinylmethyl) guanidine A suspension of the title A compound of Example 7 (1.0 g, 2.76 mmol) in isopropanol (5 ml) was treated at room temperature with 2-(aminomethyl)pyridine (1.0 ml). The reaction mixture was allowed to stir at room temperature for 4 hours and then heated under reflux for 16 hours. It was concentrated in vacuo and purified by flash chromatography eluting with ethyl acetate (2 L) followed by 10% methanol in chloroform (1 L) to yield 0.8 g of a colorless residue which was triturated from isopropyl ether to give the title compound (0.54 g) as a white solid, m.p. 202°-203° C. $^1$H NMR (DMSO) δ 8.59 (d, J=7.4 Hz, 1H), 7.79 (m, 1H), 7.60 (m, 2H), 7.36 (m, 2H), 6.91 (d, J=8.8 Hz, 1H), 5.86 (s, 1H), 4.87 (br s, 1H), 4.48 (m, 2H), 3.73 (br s, 1H), 1.40 (s, 3H), 1.18 (s, 3H). $^{13}$C NMR δ 160.8, 156.2, 148.8, 136.8, 132.8, 132.7, 124.8, 122.3, 121.2, 119.2, 117.8, 102.6, 80.4, 70.8, 51.4, 45.8, 26.6, 18.7. IR (KBr) 1439.3, 1488.6, 1592.9, 2172.4, 2226.4, 2938.9, 2980.9, 3437.2 cm$^{-1}$.

Analysis calc'd for C$_{20}$H$_{20}$N$_6$O$_2$.0.2 H$_2$O:
C, 63.22; H, 5.41; N, 22.12;
Found: C, 63.51; H, 5.36; N, 21.81.

EXAMPLE 33

(trans)-N-(2-Chlorophenyl)-N''-cyano-N-(6-cyano-3,4-dihydro-3-hydroxy-2,2-dimethyl-2H-1-benzopyran-4-yl)guanidine

A. N-Cyano-N'-(2-chlorophenyl)thiourea

The suspension of monosodium cyanamide (1.9 g, 29.4 mmol) in absolute ethanol (50 mL) was slowly treated with 2-chlorophenylisothiocyanate (5.0 g, 29.4 mmol). The reaction was allowed to stir at room temperature for 1 hour and then heated at 75° C. for 4 hours. The reaction was cooled to room temperature and the colorless solid was filtered and washed with ethanol to give the title A compound (6.0 g), m.p. 253°-255° C.

B.
(trans)-N-(2-Chlorophenyl)-N''-cyano-N-(6-cyano-3,4-dihydro-3-hydroxy-2,2-dimethyl-2H-1-benzopyran-4-yl)guanidine The solution of the title A compound (1.26 g, 5.96 mmol) and (trans)-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.* 1986, 29, 2194) in dimethylformamide (5 mL) under argon was treated with 1-(3-dimethylaminopropyl)-2-ethylcarbodiimide hydrochloride (1.17 g, 5.96 mmol). The reaction was stirred at room temperature for 2 hours and then partitioned between 1N hydrogen chloride and ethyl acetate. The aqueous phase was reextracted with ethyl acetate and the combined extracts were washed with water, sodium bicarbonate and brine. After drying over anhydrous magnesium sulfate, the solvent was evaporated and the residue was crystallized from ethyl acetate to yield 1.1 g of the title compound, m.p. 239°-240° C. $^1$H NMR (DMSO-d$_6$) δ 9.20 (s, 1H), 7.63 (d, J=8.0 Hz, 2H), 7.55 (d, J=10.0 Hz, 2H), 7.38 (m, 2H), 6.92 (d, J=9.0 Hz, 1H), 5.8 (br s, 1H), 4.91 (t, J=9.4 & 8.8 Hz, 1H), 3.68 (m, 1H), 1.39, 1.17 (s, 3H each). $^{13}$C NMR (DMSO-d$_6$) δ 159.3, 156.3, 132.6, 129.8, 128.0, 124.7, 119.0, 117.9, 116.7, 102.6, 80.5, 26.6, 18.6. IR (KBr) 3432.4, 2982.6, 2225.3 2187.9, 1611 0, 1588.7, 1491.4, 1448.1, 1267.9 cm$^{-1}$.

Analysis calc'd for C$_{20}$H$_{18}$ClN$_5$O$_2$.0.33 H$_2$O:
C, 59.79; H, 4.68; N, 17.43; Cl, 8.82;
Found: C, 60.11; H, 4.79; N, 17.21; Cl, 9.04.

EXAMPLE 34

(trans)-N-(3-Chlorophenyl)-N''-cyano-N-(6-cyano-3,4-dihydro-3-hydroxy-2,2-dimethyl-2H-1-benzopyran-4-yl)guanidine

A. N-Cyano-N'-(3-chlorophenyl)thiourea

The suspension of monosodium cyanamide (1.9 g, 29.4 mmol) in absolute ethanol (50 mL) was slowly treated with 3-chlorophenylisothiocyanate (5.0 g, 29.4 mmol). The reaction was allowed to stir at room temperature for 1 hour and then heated at 75° C. for 4 hours. The reaction was cooled to room temperature and the colorless solid was filtered and washed with ethanol to give the title A compound (5.4 g), m.p. 258°-260° C.

B.
(trans)-N-(3-chlorophenyl)-N''-cyano-N-(6-cyano-3,4-dihydro-3-hydroxy-2,2-dimethyl-2H-1-benzopyran-4-yl)guanidine The solution of the title A compound (1.26 g, 5.96 mmol) and (trans)-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.* 1986, 29, 2194) in dimethylformamide (5 mL) under argon was treated with 1-(3-dimethylaminopropyl)-2-ethylcarbodiimide hydrochloride (1.17 g, 5.96 mmol). The reaction was stirred at room temperature for 2 hours and then partitioned between 1N hydrogen chloride and ethyl acetate. The aqueous phase was reextracted with ethyl acetate and the combined extracts were washed with water, sodium bicarbonate and brine. After drying over anhydrous magnesium sulfate, the solvent was evaporated in vacuo and the residue was crystallized from ethyl acetate to yield 0.9 g of the title compound, m.p. 243°-244° C. $^1$H NMR (DMSO-d$_6$) δ 9.42 (s, 1H), 7.80 (d, J=8.8 Hz, 1H), 7.61 (d, J=8.8 Hz, 2H), 7.31 (m, 3H), 6.91 (d, J=8.8 Hz, 1H), 5.90 (br s, 1H), 4.98 (t, J=9.4 & 8.8 Hz, 1H), 3.69 (m, 1H), 1.41, 1.18 (s, 3H each). $^{13}$C NMR (DMSO-d$_6$) δ 159.0, 156.3, 139.3, 133.1, 132.7, 130.5, 124.5, 124.3, 123.1, 121.9, 119.1, 117.9, 116.8, 102.7, 80.4, 71.0, 52.0, 26.6, 18.6. IR (KBr) 3422.4, 2980.7, 2226.5, 2181.8, 1609.3, 1575.3, 1490.1, 1385.6, 1268.1 1126.5 cm$^{-1}$.

Analysis calc'd for C$_{20}$H$_{18}$ClN$_5$O$_2$.0.08 H$_2$O:
C, 60.46; H. 4.61; N, 17.63; Cl, 8.92;
Found: C, 60.11; H, 4.42; N, 17.98; Cl, 9.13.

EXAMPLE 35

(trans)-N-(4-Fluorophenyl)-N''-cyano-N-(6-cyano-3,4-dihydro-3-hydroxy-2,2-dimethyl-2H-1-benzopyran-4-yl)guanidine

A. N-Cyano-N'-(4-fluorophenyl)thiourea

The suspension of monosodium cyanamide (2.1 g, 32.6 mmol) in absolute ethanol (50 mL) was slowly treated with 4-fluorophenylisothiocyanate (5.0 g, 32.6 mmol). The reaction was allowed to stir at room temperature for 1 hour and then heated at 75° C. for 4 hours. The reaction was cooled to room temperature and the colorless solid was filtered and washed with ethanol to give the title A compound (4.1 g), m.p. >270° C.

B. (trans)-N-(4-fluorophenyl)-N''-cyano-N-(6-cyano-3,4-dihydro-3-hydroxy-2,2-dimethyl-2H-1-benzopyran-4-yl)guanidine The solution of the title A compound (1.15 g, 6.0 mmol) and (trans)-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.* 1986, 29, 2194) in dimethylformamide (5 mL) under argon was treated with 1-(3-dimethylaminopropyl)-2-ethylcarbodiimide hydrochloride (1.15 g, 6.0 mmol). The reaction was stirred at room temperature for 2 hours and then partitioned between 1N hydrogen chloride and ethyl acetate. The aqueous phase was reextracted with ethyl acetate and the combined extracts were washed with water, sodium bicarbonate and brine. After drying over anhydrous magnesium sulfate, the solvent was evaporated and the residue was triturated with ethyl acetate to yield 0.8 g of the title compound, m.p. 207°-208° C. $^1$H NMR (DMSO-$d_6$) δ 9.29 (s, 1H), 7.60 (m, 3H), 7.37 (m, 2H), 7.23 (m, 2H), 6.90 (d, J=8.8 Hz, 1H), 5.90 (br s, 1H), 4.90 (t, J=9.4 & 8.8 Hz, 1H), 3.69 (m, 1H), 1.40, 1.17 (s, 3H each). $^{13}$C NMR (DMSO-$d_6$) δ 159.4, 156.3, 133.6, 132.7, 132.5, 126.7, 126.6, 124.8, 119.1, 117.9, 115.8, 115.5, 102.6, 80.4, 70.8, 51.8, 26.6, 18.6. IR (KBr) 3412.9, 2980.5, 2226.9, 2179.4, 1611.4, 1585.5, 1509.9, 1490.6, 1385.4, 1268.2 cm$^{-1}$.

Analysis calc'd for $C_{20}H_{18}FN_5O_2 \cdot 0.15\ H_2O$:

C, 62.86; H, 4.83; N, 18.32; F, 5.01;

Found: C, 62.89; H, 4.80; N, 18.29; F, 4.84.

EXAMPLE 36

(trans)-N-[3-(Acetyloxy)-6-cyano-3,4-dihydro-2,2-dimethyl-2H-1-benzopyran-4yl]-N'-phenylguanidine The solution of the title compound from Example 3 (2.52 g, 6.98 mmoles) and acetic anhydride (1.0 g, 9.8 mmoles) in pyridine (25 ml) was stirred for 60 hours at room temperature. The crude reaction mixture was partitioned between ethyl acetate and 5% aqueous hydrogen chloride. The organic layer was washed with distilled water, saturated sodium hydrogen carbonate solution, saturated sodium chloride solution, and dried over anhydrous magnesium sulfate. The solvent was recovered under vacuum to obtain 2.97 g of a white solid. The crude reaction product was recrystallized from ethanol in two crops to obtain 2.24 g of the title compound as a pure white solid, m.p. 239°-240° C. $^1$H NMR (DMSO-$d_6$) δ 9.36 (s, 1H), 7.63 (m, 3H), 7.35 (m, 2H), 7.20 (m, 3H), 6.97 (d, J=8.80 Hz, 1H), 5.23 (m, 2H), 2.17 (s, 3H), 1.34 (s, 3H), 1.25 (s, 3H). $^{13}$C NMR (DMSO-$d_6$) δ 169.69, 158.69, 155.75, 136.95, 132.94, 132.66, 129.03, 125.28, 124.25, 123.79, 118.86, 118.09, 116.62, 103.31, 78.43, 72.07, 49.49, 25.85, 20.67, 19.54.

Analysis calc'd for $C_{22}H_{21}N_5O_3$:

C, 65.50; H, 5.25; N, 17.36;

Found: C, 65.54; H, 5.27; N, 17.36.

EXAMPLE 37

(3S-trans)-N''-Cyano-N-(6-cyano-3,4-dihydro-3-hydroxy-2,2-dimethyl-2H-1-benzopyran-4-yl)-N'-(4-fluorophenyl) guanidine The solution of N-cyano-N'-(4-fluorophenyl)thiourea (1.15 g, 6.0 mmol, prepared according to Example 35, part A) and (3S-trans)-4-amino-3,4-dihydro-3-hydroxy-2,2-dimethyl-2H-1-benzopyran-6-carbonitrile (1.0 g, 4.59 mmol, compound of Example 20, part B) in dimethylformamide (5 mL) under argon was treated with 1-(3-dimethylaminopropyl)-2-ethylcarbodiimide hydrochloride (1.15 g, 6.0 mmol). The reaction was stirred at room temperature for 2 hours and then partitioned between 1N hydrochloric acid and ethyl acetate. The aqueous phase was reextracted with ethyl acetate and the combined extracts were washed with water, sodium bicarbonate and brine. After drying over anhydrous magnesium sulfate, the solvent was evaporated and the residue was flash chromatographed on silica gel eluting with 20% hexanes in ethyl acetate to yield a colorless solid (0.55 g). This solid was triturated with ethyl ether to give the title compound (0.45 g), m.p. 218°-219° C.: $^1$H NMR (DMSO-$d_6$) δ 9.29 (s, 1H), 7.60 (m, 3H), 7.37 (m, 2H), 7.23 (m, 2H), 6.90 (d, J=8.8 Hz, 1H), 5.90 (br s, 1H), 4.90 (t, J=9.4 & 8.8 Hz, 1H), 3.69 (m, 1H), 1.40, 1.17 (s, 3H each); $^{13}$C NMR (DMSO-$d_6$) 159.4, 156.3, 133.6, 132.7, 132.5, 126.7, 126.6, 124.8, 119.1, 117.9, 115.8, 115.5, 102.6, 80.4, 70.8, 51.8, 26.6, 18.6; IR (KBr) 3412.9, 2980.5, 2226.9, 2179.4, 1611.4, 1585 5, 1509.9, 1490.6, 1385.4, 1268.2 cm$^{-1}$. $[\alpha_D]^{25} = -33.1°$ (c=0.483, MeOH).

Analysis calc'd for $C_{20}H_{18}FN_5O_2$:

C, 63.32; H, 4.78; N, 18.46; F, 5.01;

Found: C, 63.08; H, 4.94; N, 18.08; F, 4.88.

EXAMPLE 38

(3S-trans)-N-(4-Chlorophenyl)-N''-cyano-N'-(6-cyano-3,4-dihydro-3-hydroxy-2,2-dimethyl-2H-1-benzopyran-4-yl)guanidine The solution of N-cyano-N'-(4-chlorophenyl)thiourea (1.26 g, 5 96 mmol, prepared according to Example 31, part A) and (3S-trans)-4-amino-3,4-dihydro-3-hydroxy-2,2-dimethyl-2H-1-benzopyran-6-carbonitrile (1.0 g, 4.59 mmol, compound of Example 20, part B) in dimethylformamide (5 mL) under argon was treated with 1-(3-dimethylaminopropyl)-2-ethylcarbodiimide hydrochloride (1.14 g, 5.96 mmol). The reaction was stirred at room temperature for 2 hours and then partitioned between 1N hydrochloric acid and ethyl acetate. The aqueous phase was reextracted with ethyl acetate and the combined extracts were washed with water, sodium bicarbonate and brine. After drying over anhydrous magnesium sulfate, the solvent was evaporated and the residue was purified by flash chromatography eluting with a mixture of ethyl acetate/hexanes (8:2) to yield a solid (0.6 g). This solid was triturated with ethyl ether to give the title compound (0.48 g), m.p. 170°-172° C.: $^1$H NMR (DMSO-$d_6$) δ 9.43 (s, 1H), 7.68 (m, 3H), 7.45 (m, 4H), 6.95 (d, J=8.8 Hz, 1H), 5.99 (br s, 1H), 4.98 (t, J=9.4 & 8.8 Hz, 1H), 3.79 (m, 1H), 1.50, 1.27 (s, 3H each); $^{13}$C NMR (DMSO-d$_6$) 159.1, 156.2, 136.5, 132.6, 132.5, 128.8, 125.5, 124.6, 119.0, 117.8, 116.8, 102.6, 80.4, 70.9, 51.9, 26.5, 18.5; IR (KBr) 3400.7, 2226.0, 2181.6, 1606.8, 1575.9, 1491.1, 1267.3 cm$^{-1}$. [$\alpha_D$]$^{25}$ = −32.9° (c=0.492, MeOH).

Analysis calc'd for C$_{20}$H$_{18}$ClN$_5$O$_2$.0.17 H$_2$O:
C, 60.21; H. 4.64; N, 17.55; Cl, 8.89;
Found: C, 60.49; H, 4.80; N, 17.27; Cl, 8.90.

EXAMPLE 39

(3S-trans)-N-(3-Chlorophenyl)-N'''-cyano-N'-(6-cyano-3,4-dihydro-3-hydroxy-2,2-dimethyl-2H-1-benzopyran-4-yl)guanidine The solution of N-cyano-N'-(3-chlorophenyl)thiourea (1.26 g, 5.96 mmol, prepared according to Example 34, part A) and (3S-trans)-4-amino-3,4-dihydro-3-hydroxy-2,2-dimethyl-2H-1-benzopyran-6-carbonitrile (1.0 g, 4.59 mmol, compound of Example 20, part B) in dimethylformamide (5 mL) under argon was treated with 1-(3-dimethylaminopropyl)-2-ethylcarbodiimide hydrochloride (1.17 g, 5.96 mmol). The reaction was stirred at room temperature for 2 hours and then partitioned between 1N hydrochloric acid and ethyl acetate. The aqueous phase was reextracted with ethyl acetate and the combined extracts were washed with water, sodium bicarbonate and brine. After drying over anhydrous magnesium sulfate, the solvent was evaporated in vacuo and the residue was flash chromatographed on silica gel eluting with 20% hexanes in ethyl acetate to yield a colorless solid (1.0 g). This solid was recrystallized from ethyl acetate to give the title compound (0.36 g), m.p. 239°-240° C.: $^1$H NMR (DMSO-d$_6$) δ 9.42 (s, 1H), 7.80 (d, J=8.8 Hz, 1H), 7.61 (d, J=8.8 Hz, 2H), 7.31 (m, 3H), 6.91 (d, J=8.8 Hz, 1H), 5.90 (br s, 1H), 4.98 (t, J=9.4 & 8.8 Hz, 1H), 3.69 (m, 1H), 1.41, 1.18 (s, 3H each); $^{13}$C NMR (DMSO-d$_6$) 159.0, 156.3, 139.3, 133.1, 132.7, 130.5, 124.5, 124.3, 123.1, 121.9, 119.1, 117.9, 116.8, 102.7, 80.4, 71.0, 52.0, 26.6, 18.6; IR (KBr) 3422.4, 2980.7, 2226.5, 2181.8, 1609.3, 1575.3, 1490.1, 1385.6, 1268.1, 1126.5 cm$^{-1}$.[$\alpha_D$]$^{25}$ = −45.8° (c=0.45, Dimethylformamide).

Analysis calc'd for C$_{20}$H$_{18}$ClN$_5$O$_2$.0.06 H$_2$O:
C, 60.52; H, 4.60; N, 17.65; Cl, 8.93;
Found: C, 60.25; H, 4.34; N, 17.92; Cl, 9.29.

EXAMPLE 40 trans-N'''-Cyano-N-(6-cyano-3,4-dihydro-3-hydroxy-2,2-dimethyl-2H-1-benzopyran-4-yl)-N'-[4-(phenylmethoxy)phenyl)guanidine A. N-Cyano-N'-(4-phenylmethoxyphenyl)thiourea The suspension of monosodium cyanamide (1.33 g, 20.7 mmol) in absolute ethanol (50 mL) was slowly treated with 4-phenylmethoxyphenylisothiocyanate (5.0 g, 20.7 mmol). The reaction was allowed to stir at room temperature for 1 hour and then heated at 75° C. for 4 hours. The reaction was cooled to room temperature and the colorless solid was filtered and washed with ethanol to give the title A compound (4.0 g), m.p. >270° C.

B. trans-N'''-Cyano-N-(6-cyano-3,4-dihydro-3-hydroxy-2,2-dimethyl-2H-1-benzopyran-4-yl)-N'-[4-(phenylmethoxy)phenyl)guanidine The solution of the title A compound (1.68 g, 6.0 mmol) and trans-4-amino-3,4-dihydro-3-hydroxy-2,2-dimethyl-2H-1-benzopyran-6-carbonitrile (1.0 g, 4.59 mmol, prepared according to Evans et al., *J. Med. Chem.*, 1983, 26, 1582 and *J. Med. Chem.*, 1986, 29, 2194) in dimethylformamide (5 mL) under argon was treated with 1-(3-dimethylaminopropyl)-2-ethylcarbodiimide hydrochloride (1.15 g, 6.0 mmol). The reaction was stirred at room temperature for 2 hours and then partitioned between 10% citric acid and ethyl acetate and the solid was separated out. The aqueous phase was reextracted with ethyl acetate and the combined extracts were washed with water, sodium bicarbonate and brine. After drying over anhydrous magnesium sulfate, the solvent was evaporated and the residue was combined with previous solid and crystallized from hot ethyl acetate to give the title compound as a colorless solid (1.1 g), m.p. 229°-230° C.: $^1$H NMR (DMSO-d$_6$) δ 9.13 (s, 1H), 7.62 (m, 2H), 7.37 (m, 6H), 7.24 (d, J=8.8 Hz, 2H), 7.0 (d, J=8.8 Hz, 2H), 6.89 (d, J=8.2 Hz, 1H), 5.85 (br s, 1H), 5.1 (s, 2H), 4.90 (t, J=9.0 Hz, 1H), 3.69 (m, 1H), 1.40, 1.16 (s, 3H each); $^{13}$C NMR (DMSO-d$_6$) 9.6, 156.3, 137.0, 132.6, 132.4, 128.5, 127.9, 127.7, 126.6, 125.0, 119.1, 117.8, 117.3, 115.2, 102.6, 80.4, 70.6, 69.4, 51.6, 26.6, 18.6; IR (KBr) 78.0, 2936.0, 2226.3, 2180.7, 1610.0, 1581.3, 1510.9, 1489.7, 1267.5, 1238.5 cm$^{-1}$.

Analysis calc'd for C$_{27}$H$_{25}$N$_5$O$_3$.0.34 H$_2$O:
C, 68.47; H, 5.46; N, 14.79;
Found: C, 68.55; H, 5.34; N, 14.71.

EXAMPLE 41 trans-N'''-Cyano-N-(6-cyano-3,4-dihydro-3-hydroxy-2,2-dimethyl-2H-1-benzopyran-4-yl)-N'-(4-hydroxyphenyl)guanidine To a solution of the title compound from Example 40 (0.7 g, 1.5 mmol) in ethanol (70 mL) was added (10%) palladium on carbon (0.1 g). It was then treated with hydrogen in a balloon and heated at 60° C. for 2 hours. The reaction was filtered through a pad of celite, the filtrate was washed with ethanol and concentrated in vacuo to give the title compound as a colorless solid (0.5 g), m.p. 171°-173° C.: $^1$H NMR (DMSO-d$_6$) δ 9.40 (s, 1H), 9.03 (s, 1H), 7.58 (d, J=8.2 Hz, 1H), 7.51 (s, 2H), 7.2 (s, 1H), 7.11 (d, J=8.8 Hz, 2H), 6.89 (d, J=8.2 Hz, 1H), 6.73 (d, J=8.8 Hz, 2H), 5.85 (br s, 1H), 4.87 (t, J=9.0 Hz, 1H), 3.71 (m, 1H), 1.38, 1.15 (s, 3H each); $^{13}$C NMR (DMSO-d$_6$) 159.6, 156.3, 132.6, 132.4, 127.0, 126.6, 119.1, 117.8, 117.3, 115.6, 102.6, 80.4, 79.4, 70.6, 51.6, 26.7, 18.6; IR (KBr) 3485.6, 2986.0, 2941.6, 2226.0, 1585.6, 1514.2, 1491.1, 1307.8, 1271.2, 1128.4 cm$^{-1}$.

Analysis calc'd for C$_{20}$H$_{19}$N$_5$O$_3$.0.4 H$_2$O:
C, 62.46; H, 5.19; N, 18.21;
Found: C, 62.71; H, 5.17; N, 17.96.

EXAMPLE 42 trans-N-(6-Acetyl-3,4-dihydro-3-hydroxy-2,2-dimethyl-2H-1-benzopyran-4-yl)-N'''-cyano-N'-phenylguanidine The solution of N-cyano-N'-phenylthiourea (0.98 g, 5.5 mmol, compound of Example 3, part A) and 6-acetyl-3,4-dihydro-2,2-dimethyl-3-hydroxy-4-amino-2H-1-benzopyran (1.0 g, 4.25 mmol, prepared according to Evans et al., *J. Med. Chem.*, 1983, 26, 1582 and *J. Med. Chem.*, 1986, 29, 2194) in dimethylformamide (6 ml) under argon was treated with 1-(3-dimethylaminopropyl)-2-ethylcarbodiimide hydrochloride (1.1 g, 5.5 mmol). The reaction was stirred at room temperature for 2 hours and then partitioned between 10% citric acid and ethyl acetate. The aqueous phase was reextracted with ethyl acetate and the combined extracts were washed with water, sodium bicarbonate and brine. After drying over anhydrous magnesium sulfate, the solvent was evaporated and the residue was crystallized from ethyl acetate to yield the title compound (0.43 g), m.p. 182°–184° C.: $^1$H NMR (DMSO-d$_6$) δ 9.45 (s, 1H), 7.82 (m, 3H), 7.44 (s, 3H), 7.25 (s, 1H), 6.96 (d, J=9.0 Hz, 1H), 6.0 (s, 1H), 5.1 (m, 1H), 4.15 (m, 1H), 3.8 (s, 1H), 2.61 (s, 3H), 1.52 (s, 3H), 1.29 (s, 3H); $^{13}$C NMR (CDCl$_3$) δ 196.2, 159.3, 156.6, 137.6, 129.7, 129.1, 128.4, 124.7, 123.5, 123.3, 117.2, 116.6, 80.0, 71.2, 52.3, 26.7, 26.3, 18.6; IR (KBr) 3412.3, 2978.3, 2935.8, 2179.7, 1670.5, 1602.9, 1577.9, 1493.0, 1359.9, 1271.2, 1126.5 cm$^{-1}$.

Analysis calc'd for C$_{21}$H$_{22}$N$_4$O$_3$.0.57 H$_2$O:
C, 64.89; H, 6.00; N, 14.41;
Found: C, 65.23; H, 6.11; N, 13.98.

EXAMPLE 43

(3S-trans)-N-(3,4-Dichlorophenyl)-N''-cyano-N'-(6-cyano-3,4-dihydro-3-hydroxy-2,2-dimethyl-2H-1-benzopyran-4-yl)guanidine A. N-Cyano-N'-(3,4-dichlorophenyl)thiourea The suspension of monosodium cyanamide (1.6 g, 24.5 mmol) in absolute ethanol (50 mL) was slowly treated with 3,4-dichlorophenylisothiocyanate (5.0 g, 24.5 mmol). The reaction was allowed to stir at room temperature for 1 hour and then heated at 75° C. for 4 hours. The reaction was cooled to room temperature and the colorless solid was filtered and washed with ethanol to give the title A compound (5.0 g) as a colorless solid.

B.
(3S-trans)-N-(3,4-Dichlorophenyl)-N''-cyano-N'-(6-cyano-3,4-dihydro-3-hydroxy-2,2-dimethyl-2H-1-benzopyran-4-yl)guanidine The solution of the title A compound (1.47 g, 6.0 mmol) and (3S-trans)-4-amino-3,4-dihydro-3-hydroxy-2,2-dimethyl-2H-1-benzopyran-6-carbonitrile (1.0 g, 4.6 mmol, compound of Example 20, part B) in dimethylformamide (10 mL) under argon was treated with 1-(3-dimethylaminopropyl)-2-ethylcarbodiimide hydrochloride (1.13 g, 6.0 mmol). The reaction was stirred at room temperature for 2 hours and then partitioned between pH 4 buffer and ethyl acetate. The aqueous phase was reextracted with ethyl acetate and the combined extracts were washed with water (4×200 ml), sodium bicarbonate and brine. After drying over anhydrous magnesium sulfate, the solvent was evaporated and the residue was purified by flash chromatography (ethyl acetate:hexanes/7:3) to yield a colorless solid (0.6 g). The solid was triturated with ethyl ether to give the title compound (0.5 g), m.p. 168°–170° C.: $^1$H NMR (CDCl$_3$) δ 9.30 (s, 1H), 7.64 (s, 1H), 7.58 (d, J=2.4 Hz, 1H), 7.40 (m, 2H), 7.30 (dd, J=2.3 & 2.9, 1H), 6.85 (d, J=8.8 Hz, 1H), 4.97 (m, 1H), 3.70 (d, J=10.0 Hz, 1H), 1.49, 1.26 (s, 3H each); $^{13}$C NMR (CDCl$_3$) 158.6, 155.8, 136.4, 131.9, 131.4, 129.7, 118.1, 117.3, 102.6, 79.6, 51.8, 25.8, 17.8; IR (KBr) 3398, 2980, 2225, 2183, 1610, 1581, 1489, 1371 cm$^{-1}$. [α$_D$]$^{25}$ = −35.37° (c=0.458, dimethylformamide).

Analysis calc'd for C$_{20}$H$_{17}$Cl$_2$N$_5$O$_2$.0.37 H$_2$O:
C, 54.97; H, 4.09; N, 16.02; Cl, 16.22;
Found: C, 55.39; H, 4.04; N, 15.60; Cl, 15.97.

EXAMPLE 44

(3S-trans)-N''-Cyano-N-(6-cyano-3,4-dihydro-3-hydroxy-2,2-dimethyl-2H-1-benzopyran-4-yl)-N'-[4-(trifluoromethyl)phenyl)]guanidine A. N-Cyano-N'-(4-trifluoromethylphenyl)thiourea The suspension of monosodium cyanamide (0.63 g, 9.8 mmol) in absolute ethanol (50 mL) was slowly treated with 4-trifluoromethylphenylisothiocyanate (2.0 g, 9.8 mmol). The reaction was allowed to stir at room temperature for 1 hour and then heated at 75° C. for 4 hours. The reaction was cooled to room temperature and the colorless solid was filtered and washed with ethanol to give the title compound (2.0 g) as a colorless solid.

B.
(3S-trans)-N''-Cyano-N-(6-cyano-3,4-dihydro-3-hydroxy-2,2-dimethyl-2H-1-benzopyran-4-yl)-N'-[4-(trifluoromethyl)phenyl)]guanidine The solution of the title A compound (1.3 g, 5.3 mmol) and (3S-trans)-4-amino-3,4-dihydro-3-hydroxy-2,2-dimethyl-2H-1-benzopyran-6-carbonitrile (0.83 g, 3.8 mmol, prepared according to Example 20, part B) in dimethylformamide (10 mL) under argon was treated with 1-(3-dimethylaminopropyl)-2-ethylcarbodiimide hydrochloride (1.1 g, 5.7 mmol). The reaction was stirred at room temperature for 2 hours and then partitioned between pH 4 buffer and ethyl acetate. The aqueous phase was reextracted with ethyl acetate and the combined extracts were washed with water (4×200 ml), sodium bicarbonate and brine. After drying over anhydrous magnesium sulfate, the solvent was evaporated and the residue was purified by flash chromatography eluting with a mixture of ethyl acetate/hexanes (7:3). The solid was triturated with ethyl ether to give the title compound (0.45 g), m.p. 209°–210° C.: $^1$H NMR (CDCl$_3$) δ 9.41 (s, 1H), 7.60 (m, 6H), 6.85 (d, J=8.8 Hz, 1H), 4.99 (m, 1H), 3.74 (d, J=9.4 Hz, 1H), 1.50, 1.28 (s, 3H each); $^{13}$C NMR (CDCl$_3$) 158.7, 156.0, 140.4, 132.1, 125.5, 123.9, 121.9, 118.3, 117.5, 102.8, 79.8, 52.1, 25.9, 18.0; IR (KBr) 3403, 2226, 2184, 1588, 1491, 1325, 1126, 1069 cm$^{-1}$. [α$_D$]$^{25}$ = −40.2 (c=0.567, MeOH).

Analysis calc'd for C$_{21}$H$_{18}$F$_3$N$_5$O$_2$:
C, 58.74; H, 4.23; N, 16.31; F, 13.27;
Found: C, 59.15; H, 4.16; N, 16.18; F, 13.53.

What is claimed is:

1. A compound of the formula

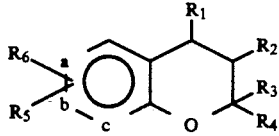

wherein a, b, and c are all carbons or one of a, b and c is nitrogen or —NO— and the others are carbons;

$R_1$ is 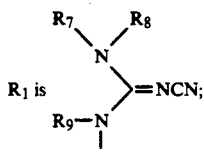 =NCN;

R$_2$ is hydrogen, hydroxy or $$-\underset{\underset{O}{\|}}{O}CCH_3$$

R$_3$ and R$_4$ are each independently hydrogen, alkyl or arylalkyl, or, R$_3$ and R$_4$ taken together with the carbon atoms to which they are attached form a 5- to 7-membered carbocyclic ring;

R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S—alkyl, —SOalkyl, —SO$_2$alkyl, $$-P(O\text{-alkyl})_2, \quad \overset{O}{\underset{O}{\|}}P\overset{O}{\underset{O}{\diagup}}\left\{\begin{matrix}\\\\\end{matrix}\right\}_n-R,$$

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups is hydrogen, alkyl, haloalkyl, aryl, arylalkyl, cycloalkyl, or (cycloalkyl)alkyl;

R$_6$ is selected from H, alkyl, OH, O-alkyl, amino, substituted amino, NHCOR (wherein R is as defined above), CN, and NO$_2$;

R$_7$ is selected from aryl, heterocyclo and (heterocyclo)alkyl;

R$_8$ is selected from hydrogen, alkyl, aryl, alkenyl and arylalkyl;

R$_9$ is selected from hydrogen, alkyl, alkenyl, aryl, arylalkyl, cycloalkyl or cycloalkylalkyl;

n is 1, 2 or 3; and, wherein the term "aryl" refers to phenyl, 1-naphthyl, 2-naphthyl, or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, $$-CF_3, -OCHF_2, -O-CH_2-\!\!\bigcirc\!\!-R_{11},$$

$$-S-CH_2-\!\!\bigcirc\!\!-R_{11}$$

(wherein R$_{11}$ is hydrogen, alkyl of 1 to 4 carbons, alkoxy of 1 to 4 carbons, alkylthio of 1 to 4 carbons, halo, hydroxy or CF$_3$), —O—CH$_2$—cycloalkyl, or —S—CH$_2$— cycloalkyl, and di-substituted phenyl, 1-naphthyl, 2-naphthyl, wherein said substituents are selected from methyl, methoxy, methylthio, halo, CF$_3$, nitro, amino, and OCHF$_2$;

the term "heterocyclo" refers 2- and 3-thienyl, 2- and 3-furyl, 2- , 3- and 4-pyridyl, imidazolyl, 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6, or 7-benzoxazolyl, 4, 5, 6, or 7-benzimidazolyl, 4, 5, 6, or 7-benzoxadiazolyl, and 4, 5, 6, or 7-benzofuranzanyl; or such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-13 alkyl wherein alkyl is of 1 to 4 carbons, —N(alkyl)$_2$ wherein alkyl is of 1 to 4 carbons, CF$_3$, OCHF$_2$ or such monocyclic and bicyclic rings wherein two or three available carbons have substituents selected from methyl, methoxy, methylthio, halo, CF$_3$, nitro, hydroxy, amino and OCHF$_2$; and, the term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

2. A compound in accordance with claim 1 wherein R$_7$ is aryl.

3. A compound in accordance with claim 2 wherein R$_7$ is phenyl or substituted phenyl.

4. A compound in accordance with claim 1 wherein a is nitrogen or —CR$_5$;

b and c are each —CH—;

R$_2$ is trans-hydroxy;

R$_3$ and R$_4$ are each methyl;

R$_5$ is —CN or —NO$_2$;

R$_6$ is hydrogen;

R$_7$ is phenyl or substituted phenyl;

R$_8$ is hydrogen;

R$_9$ is hydrogen; and n is 1 or 2.

5. A compound in accordance with claim 1 having the formula $$\begin{array}{c}R_7-NH\\\phantom{XXX}\diagdown\\\phantom{XXX}\phantom{X}=NCN\\NC\phantom{XX}\diagup\\\phantom{XX}NH\end{array}$$

wherein R$_7$ is substituted phenyl and the substituents are selected from alkyl, cyano, alkoxy, nitro, halo, dihalo, haloalkyl, hydroxy and benzyloxy.

6. A compound in accordance with claim 1 having the name (trans)-N"-cyano-N-(6-cyano-3,4-dihydro-3-hydroxy-2,2-dimethyl-2H-1-benzopyran-4-yl)-N'-phenyl guanidine.

7. A compound in accordance with claim 1 having the name (trans)-N"-cyano-N-(3,4-dihydro-3-hydroxy-2,2-dimethyl-2H-pyrano[3,2c] pyridin-4-yl)-phenylguanidine.

8. A compound in accordance with claim 1 having the name (3S-trans)-N"-cyano-N-(6-cyano-3,4-dihydro-3-hydroxy-2,2-dimethyl-2H-1-benzopyran-4-yl)-N'-phenylguanidine.

9. A compound in accordance with claim 1 having the name (3R-trans)-N"-cyano-N-(6-cyano-3,4-dihydro- 3-hydroxy-2,2-dimethyl-2H-1-benzopyran-4-yl)-N'-phenylguanidine.

10. A compound in accordance with claim 1 having the name (trans)-N''-cyano-N-(6-cyano-3,4-dihydro-3-hydroxy-2,2-dimethyl-2H-1-benzopyran-4-yl)-N'-(4-pyridinylmethyl)guanidine.

11. A compound in accordance with claim 1 having the name (trans)-N''-cyano-N-(6-cyano-3,4-dihydro-3-hydroxy-2,2-dimethyl-2H-1-benzopyran-4-yl)-N'-(3-pyridinylmethyl)guanidine.

12. A compound in accordance with claim 1 having the name (trans)-N''-cyano-N-(6-ethynyl-3,4-dihydro-3-hydroxy-2,2-dimethyl-2H-1-benzopyran-4-yl)-N'-phenylguanidine.

13. A compound in accordance with claim 1 having the name (trans)-N''-cyano-N-(3,4-dihydro-6-(phenylethynyl)-2H-1-benzopyran-4-yl)-N'-phenylguanidine.

14. A compound in accordance with claim 1 having the name (trans)-N''-cyano-N-(3-4-dihydro-3-hydroxy-2,2-dimethyl-6-nitro-2H-1-benzopyran-4-yl)-N'-phenylguanidine.

15. A compound in accordance with claim 1 having the name (trans)-N''-cyano-N-(6-cyano-3,4-dihydro-3-hydroxy-2,2-dimethyl-2H-1-benzopyran-4-yl)-N'-(4-cyanophenyl)guanidine.

16. A compound in accordance with claim 1 having the name (trans)-N''-cyano-N-(6-cyano-3,4-dihydro-3-hydroxy-2,2-dimethyl-2H-1-benzopyran-4-yl)-N'-(4-methoxyphenyl)guanidine.

17. A compound in accordance with claim 1 having the name (trans)-N''-cyano-N-(6-cyano-3,4-dihydro-2,2-dimethyl-2H-1-benzopyran-4-yl)-N'-phenylguanidine.

18. A compound in accordance with claim 1 having the name (trans)-N''-cyano-N-(6-cyano-3,4-dihydro-3-hydroxy-2,2-dimethyl-2H-1-benzopyran-4-yl)-N'-(4-nitrophenyl)guanidine.

19. A compound in accordance with claim 1 having the name (trans)-N-(4-chlorophenyl)-N''-cyano-N-(6-cyano-3,4-dihydro-3-hydroxy-2,2-dimethyl-2H-1-benzopyran-4-yl)guanidine.

20. A compound in accordance with claim 1 having the name (trans)-N''-cyano-N-(6-cyano-3,4-dihydro-3-hydroxy-2,2-dimethyl-2H-1-benzopyran-4-yl)-N'-(2-pyridinylmethyl) guanidine.

21. A compound in accordance with claim 1 having the name (trans)-N-(2-chlorophenyl)-N''-cyano-N-(6-cyano-3,4-dihydro-3-hydroxy-2,2-dimethyl-2H-1-benzopyran-4-yl)guanidine.

22. A compound in accordance with claim 1 having the name (trans)-N-(3-chlorophenyl)-N''-cyano-N-(6-cyano-3,4-dihydro-3-hydroxy-2,2-dimethyl-2H-1-benzopyran-4-yl)guanidine.

23. A compound in accordance with claim 1 having the name (trans)-N-(4-fluorophenyl)-N''-cyano-N-(6-cyano-3,4-dihydro-3-hydroxy-2,2-dimethyl-2H-1-benzopyran-4-yl)guanidine.

24. A compound in accordance with claim 1 having the name (trans)-N-[3-(acetyloxy)-6-cyano-3,4-dihydro-2,2-dimethyl-2H-1-benzopyran-4yl]-N'-phenylguanidine.

25. A compound in accordance with claim 1 having the name (3S-trans)-N''-cyano-N-(6-cyano-3,4-dihydro-3-hydroxy-2,2-dimethyl-2H-1-benzopyran-4-yl)-N'-(4-fluorophenyl) guanidine.

26. A compound in accordance with claim 1 having the name (3S-trans)-N-(4-chlorophenyl)-N''-cyano-N''-(6-cyano-3,4-dihydro-3-hydroxy-2,2-dimethyl-2H-1-benzopyran-4-yl)guanidine.

27. A compound in accordance with claim 1 having the name (3S-trans)-N-(3-chlorophenyl)-N''-cyano-N'-(6-cyano-3,4-dihydro-3-hydroxy-2,2-dimethyl-2H-1-benzopyran-4-yl)guanidine.

28. A compound in accordance with claim 1 having the name trans-N''-cyano-N-(6-cyano-3,4-dihydro-3-hydroxy-2,2-dimethyl-2H-1-benzopyran-4-yl)-N'-[4-(phenylmethoxy)phenyl]guanidine.

29. A compound in accordance with claim 1 having the name trans-N''-cyano-N-(6-cyano-3,4-dihydro-3-hydroxy-2,2-dimethyl-2H-1-benzopyran-4-yl)-N'(4-hydroxyphenyl)guanidine.

30. A compound in accordance with claim 1 having the name trans-N-(6-acetyl-3,4-dihydro-3-hydroxy-2,2-dimethyl-2H-1-benzopyran-4-yl)-N''-cyano-N'-phenylguanidine.

31. A compound in accordance with claim 1 having the name (3S-trans)-N-(3,4-dichlorophenyl)-N''-cyano-N'-(6-cyano-3,4-dihydro-3-hydroxy-2,2-dimethyl-2H-1-benzopyran-4-yl)guanidine.

32. A compound in accordance with claim 1 having the name (3S-trans)-N''-cyano-N-(6-cyano-3,4-dihydro-3-hydroxy-2,2-dimethyl-2H-1-benzopyran-4-yl)-N'-[4-(trifluoromethyl)phenyl)]guanidine.

33. A method for the treatment of an ischemic condition in a mammalian specie comprising administering to a mammalian specie in need thereof an effective amount of a potassium channel activation of a compound having the formula

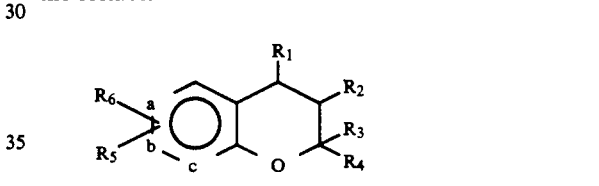

wherein a, b, and c are all carbons or one of a, b and c is nitrogen or —NO— and the others are carbons;

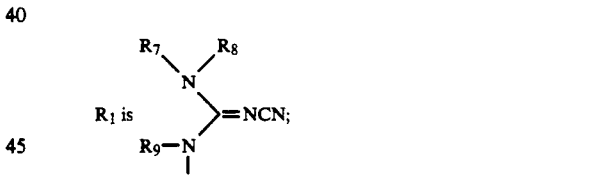

R₂ is hydrogen, hydroxy or

R₃ and R₄ are each independently hydrogen, alkyl or arylalkyl, or, R₃ and R₄ taken together with the carbon atoms to which they are attached form a 5- to 7-membered carbocyclic ring;

R₅ is selected from H, alkyl, haloalkyl, alkenyl, alkynyl, cycloalkyl, arylalkyl, cycloalkylalkyl, —CN, —NO₂, —COR, —COOR, —CONHR, —CONR₂, —CF₃, S—alkyl, —SOalkyl, —SO₂alkyl,

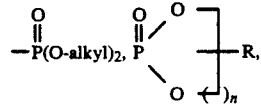

halogen, amino, substituted amino, O-alkyl, OCF$_3$, OCH$_2$CF$_3$, —OCOalkyl, —OCONRalkyl, —NR-COalkyl and NRCOOalkyl, NRCONR$_2$ wherein R in each of the above groups is hydrogen, alkyl, haloalkyl, aryl, arylalkyl, cycloalkyl, or (cycloalkyl)alkyl;

R$_6$ is selected from H, alkyl, OH, O-alkyl, amino, substituted amino, NHCOR (wherein R is as defined above), CN, and NO$_2$;

R$_7$ is selected from aryl, heterocyclo and (heterocyclo)alkyl;

R$_8$ is selected from hydrogen, alkyl, aryl, alkenyl and arylalkyl;

R$_9$ is selected from hydrogen, alkyl, alkenyl, aryl, arylalkyl, cycloalkyl or cycloalkylalkyl;

n is 1, 2 or 3; and, wherein the term "aryl" refers to phenyl, 1-naphthyl, 2-naphthyl, or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons,

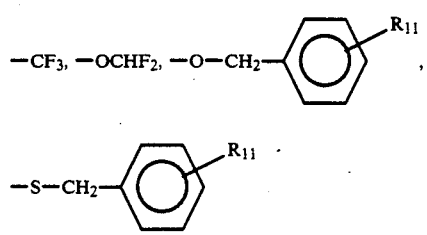

(wherein R$_{11}$ is hydrogen, alkyl of 1 to 4 carbons, alkoxy of 1 to 4 carbons, alkylthio of 1 to 4 carbons, halo, hydroxy or CF$_3$), —O—CH$_2$—cycloalkyl, or —S—CH$_2$— cycloalkyl, and di-substituted phenyl, 1-naphthyl, 2-naphthyl, wherein said substituents are selected from methyl, methoxy, methylthio, halo, CF$_3$, nitro, amino, and OCHF$_2$;

the term "heterocyclo" refers 2- and 3-thienyl, 2- and 3-furyl, 2-, 3- and 4-pyridyl, imidazolyl, 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6, or 7-benzoxazolyl, 4, 5, 6, or 7-benzimidazolyl, 4, 5, 6, or 7-benzoxadiazolyl, and 4, 5, 6, or 7-benzofuranzanyl; or such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-13 alkyl wherein alkyl is of 1 to 4 carbons, —N(alkyl)$_2$ wherein alkyl is of 1 to 4 carbons, CF$_3$, OCHF$_2$ or such monocyclic and bicyclic rings wherein two or three available carbons have substituents selected from methyl, methoxy, methylthio, halo, CF$_3$, nitro, hydroxy, amino and OCHF$_2$; and, the term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

34. The method of claim 33 wherein R$_7$ in the potassium channel activator is phenyl or substituted phenyl.

35. A pharmaceutical composition for the treatment of ischemic conditions comprising a compound of claim 1 and a pharmaceutically acceptable carrier therefor.

* * * * *